(12) United States Patent
Bardy et al.

(10) Patent No.: US 11,794,020 B2
(45) Date of Patent: Oct. 24, 2023

(54) SYSTEM AND METHOD FOR DATA EXCHANGE AND CHARGING

(71) Applicant: Bardy Diagnostics, Inc., Bellevue, WA (US)

(72) Inventors: Gust H. Bardy, Carnation, WA (US); Jason Felix, Vashon Island, WA (US); Lilly Paul, Bellevue, WA (US)

(73) Assignee: BARDY DIAGNOSTICS, INC., Bellevue, WA (US)

(*) Notice: Subject to any disclaimer, the term of this patent is extended or adjusted under 35 U.S.C. 154(b) by 0 days.

(21) Appl. No.: 17/572,436

(22) Filed: Jan. 10, 2022

(65) Prior Publication Data

US 2022/0219001 A1 Jul. 14, 2022

Related U.S. Application Data

(60) Provisional application No. 63/135,752, filed on Jan. 11, 2021.

(51) Int. Cl.
*A61N 1/372* (2006.01)
*H04W 4/80* (2018.01)
(Continued)

(52) U.S. Cl.
CPC ........ *A61N 1/37223* (2013.01); *A61B 5/0006* (2013.01); *A61B 5/0031* (2013.01); *A61B 5/686* (2013.01); *A61N 1/3787* (2013.01); *H02J 7/00032* (2020.01); *H02J 7/02* (2013.01); *H04W 4/80* (2018.02); *A61B 2560/0219* (2013.01)

(58) Field of Classification Search
CPC ......... A61N 1/37223; A61N 1/3787; A61B 5/0006; A61B 5/0031; A61B 5/686; A61B 2560/0219; A61B 5/332; A61B 5/6823; A61B 5/6833; H02J 7/00032; H02J 7/02; H04W 4/80; G16H 40/67; G16H 80/00; G16H 40/63
USPC ........................................... 320/137
See application file for complete search history.

(56) References Cited

U.S. PATENT DOCUMENTS 9,277,864 B2 * 3/2016 Yang ................. A61B 5/05
9,510,755 B2 * 12/2016 Fong ................ A61B 5/0006
(Continued)

FOREIGN PATENT DOCUMENTS

CN 109259741 A * 1/2019 .......... A61B 5/0015
WO 2010104952 9/2010
WO WO-2022094252 A1 * 5/2022 .......... A61B 5/6861

OTHER PUBLICATIONS

May 2, 2022 Letter From Counsel. 1:22-cv-00351-CFC. May 2, 2022.
(Continued)

*Primary Examiner* — M Baye Diao
(74) *Attorney, Agent, or Firm* — K&L Gates LLP

(57) ABSTRACT

A method for data exchange and charging is provided. An implantable medical device is monitored and charging of the implantable medical device is initiated by providing charge parameters to a bedside monitor. Communication is initiated between a puck associated with the bedside monitor and implantable medical device. The implantable medical device is charged using the charge parameters. Simultaneously with the charging, transfer of data between the implantable medical device and the bedside monitor is initiated.

20 Claims, 18 Drawing Sheets

(51) Int. Cl.
*H02J 7/00* (2006.01)
*A61N 1/378* (2006.01)
*H02J 7/02* (2016.01)
*A61B 5/00* (2006.01)

(56) References Cited

U.S. PATENT DOCUMENTS

| | | | |
|---|---|---|---|
| 9,634,734 | B2 | 4/2017 | Lee et al. |
| 11,096,579 | B2* | 8/2021 | Dreisbach ............ G06F 21/6245 |
| 2007/0270921 | A1 | 11/2007 | Strother et al. |
| 2016/0175600 | A1 | 6/2016 | Amir et al. |
| 2016/0199657 | A1* | 7/2016 | Jiang .................... A61N 1/3787 607/61 |
| 2018/0333585 | A1* | 11/2018 | Gaddam .............. A61N 1/3787 |
| 2019/0247669 | A1 | 8/2019 | Nielsen et al. |
| 2021/0000418 | A1* | 1/2021 | Felix ..................... A61B 5/316 |
| 2021/0378513 | A1* | 12/2021 | Dreisbach ............. G16H 40/67 |
| 2021/0401370 | A1* | 12/2021 | Taff ......................... A61B 5/74 |

OTHER PUBLICATIONS

Mao Shitong et al: "Simultaneous wireless power transfer and data communication using synchronous pulse-controlled load modulation", Meaeasurement, Institute of Measurement and Control. London, GB, vol. 109, Jun. 2, 2017 (Jun. 2, 2017), pp. 316-325, XP085123919, ISSN: 0263-2241, DOI: 10.1016/J.MEASUREMENT. 2017.05.068.
Trigui Aref et al: "Maximizing Data Transmission Rate for Implantable Devices Over a Single Inductive Link: Methodological Review", IEEE Reviews in Biomedical Engineering, vol. 12 , pp. 72-87, XP011710339, ISSN: 1937-3333, DOI: 10.1109/RBME.2018. 2873817 [retrieved on Feb. 15, 2019].
May 24, 2022 Letter to Opposing Counsel. 1:22-cv-00351-CFC. May 24, 2022.
Complaint from Case No. 1:22-cv-00351-UNA, *Bardy Diagnostics, Inc.* (Plaintiff) v. *Vital Connect, Inc.* (Defendant), Filed: Mar. 18, 2022, 182 pages.
Defendant's Opening Brief In Support of Its Motion To Dismiss For Failure to State A Claim from Case No. 1:22-cv-00351-CFC, *Bardy Diagnostics, Inc.* (Plaintiff) v. *Vital Connect, Inc.* (Defendant), Filed: May 25, 2022, 18 pages.
Defendant's Answer, Defenses, and Counterclaim from Case No. 1:22-cv-00351-CFC, *Bardy Diagnostics, Inc.* (Plaintiff) v. *Vital Connect, Inc.* (Defendant), Filed: May 25, 2022, 132 pages.
Plaintiff's Answering Brief In Opposition to Defendant's Motion to Dismiss For Failure to State a Claim from Case No. 1:22-cv-00351-CFC, *Bardy Diagnostics, Inc.* (Plaintiff) v. *Vital Connect, Inc.* (Defendant), Filed: Jun. 8, 2022, 25 pages.
Plaintiff's Answer to Defendant's Counterclaim from Case No. 1:22-cv-00351-CFC, *Bardy Diagnostics, Inc.* (Plaintiff) v. *Vital Connect, Inc.* (Defendant), Filed: Jun. 15, 2022, 5 pages.
Defendant's Reply Brief In Support of Its Motion to Dismiss For Failure to State a Claim from Case No. 1:22-cv-00351-CFC, *Bardy Diagnostics, Inc.* (Plaintiff) v. *Vital Connect, Inc.* (Defendant), Filed: Jun. 15, 2022, 93 pages.
Oct. 17, 2022 Letter to Opposing Counsel, *Bardy Diagnostics, Inc.* v. *Vital Connect, Inc.*, No. 22-cv-00351-CFC (D. Del.), Oct. 17, 2022.
Nov. 11, 2022, Letter from Opposing Counsel, 1:22-cv-00351-CJB; *Bardy Diagnostics, Inc.* v. *Vital Connect, Inc.* (D. Del ), Nov. 11, 2022.
Dec. 26, 2022 Letter from Opposing Counsel, 1:22-cv-00351-CJB; *Bardy Diagnostics, Inc.* v. *Vital Connect, Inc.* (D. Del.); and IPR2023-00381; *Vital Connect, Inc.* v. *Bardy Diagnostics, Inc.* (P.T.A.B.), Dec. 26, 2022.
First Amended Complaint for Patent Infringement, 1:22-cv-00351-CJB, *Bardy Diagnostics, Inc.* v. *Vital Connect, Inc.* (D. Del.), filed Jan. 10, 2023.
Petition for Inter Partes Review of U.S. Pat. No. 11,051,743 Pursuant to 35 U.S.C. §§ 311-319 and 37 C.F.R. § 42, Case No. IPR2023-00381, *Vital Connect, Inc.* v. *Bardy Diagnostics, Inc.* (P.T.A.B.), Dec. 21, 2022, 875 pages.
Defendant's Answer to First Amended Complaint, Defenses, and Counterclaim, 1:22-cv-00351-CJB, *Bardy Diagnostics, Inc.* v. *Vital Connect, Inc.* (D. Del.), filed Jan. 24, 2023 (227 pages).

\* cited by examiner (a)

(b)

320

430

440

450

460

SYSTEM AND METHOD FOR DATA EXCHANGE AND CHARGING

FIELD

This application relates in general to cardiac monitoring and, in particular, to a system and method for data exchange and charging.

BACKGROUND

The heart emits electrical signals as a by-product of the propagation of the action potentials that trigger depolarization of heart fibers. An electrocardiogram (ECG) measures and records such electrical potentials to visually depict the electrical activity of the heart over time. Conventionally, dermal ECG electrodes positioned on and insertable cardiac monitors (ICMs) implanted in a patient are utilized to sense cardiac electrical activity. The sensed cardiac electrical activity is represented by PQRSTU waveforms that can be interpreted post-ECG recordation to derive heart rate and physiology. The P-wave represents atrial electrical activity. The QRSTU components represent ventricular electrical activity.

An ECG is a tool used by physicians to diagnose heart problems and other potential health concerns. An ECG is a snapshot of heart function, typically recorded over 12 seconds, that can help diagnose rate and regularity of heartbeats, effect of drugs or cardiac devices, including pacemakers and implantable cardioverter-defibrillators (ICDs), and whether a patient has heart disease. ECGs are used in-clinic during appointments, and, as a result, are limited to recording only those heart-related aspects present at the time of recording. Sporadic conditions that may not show up during a spot ECG recording require other means to diagnose them. These disorders include fainting or syncope; rhythm disorders, such as tachyarrhythmias and bradyarrhythmias; apneic episodes; and other cardiac and related disorders. Thus, an ECG only provides a partial picture and can be insufficient for complete patient diagnosis of many cardiac disorders.

Long term monitoring of a patient via a dermal cardiac device or ICM can provide a larger picture of a patient's cardiac activity, such as over a time span of 7 days or more, which can be helpful to identify conditions and disorders that are not generally viewed during a spot ECG recording. However, the data recorded by the dermal cardiac device or ICM is generally accessed by a medical professional after a scheduled data transmission which can be hours or days later.

Typically, data is downloaded from the device at preset intervals. To download the data, a wand or other device is placed over the patient's cardiac device to access the stored data, such as via a wireless connection. The accessed data can then be stored and processed. However, since the cardiac data is collected at a predetermined time such data is generally not useful to identify or diagnose a condition or disorder of the patient, unless the patient is in the office or medical facility.

Remote real-time views of the cardiac data can be useful in treating a patient, such as when a patient experiences a cardiac event. For example, after a patient experiences a cardiac event, such as palpitations, the patient can contact his physician or an alert can be delivered to the physician that a cardiac event has occurred. The physician can then review the patient's cardiac activity in real-time to determine whether the patient needs additional care or should go to the hospital.

While some conventional cardiac monitors, both dermal and ICMs, include wireless data transmission, such devices do not allow for real-time streaming of cardiac data from the device to a remote computer. As described above, the cardiac data collected by the cardiac monitor is generally retrieved via a wand on a tablet or other computer. Each time the computer communicates with the server.

Therefore, a need remains for remote real-time streaming of cardiac data and designated pathways for communication of ECG and parameter data to and from the implantable medical device.

SUMMARY

Physiological monitoring can be provided through a wearable monitor that includes two components, a flexible extended wear electrode patch and a removable reusable monitor recorder. The wearable monitor sits centrally (in the midline) on the patient's chest along the sternum oriented top-to-bottom. The placement of the wearable monitor in a location at the sternal midline (or immediately to either side of the sternum), with its unique narrow "hourglass"-like shape, benefits long-term extended wear by removing the requirement that ECG electrodes be continually placed in the same spots on the skin throughout the monitoring period. Instead, the patient is free to place an electrode patch anywhere within the general region of the sternum. In addition, power is provided through a battery provided on the electrode patch, which avoids having to either periodically open the housing of the monitor recorder for the battery replacement, which also creates the potential for moisture intrusion and human error, or to recharge the battery, which can potentially take the monitor recorder off line for hours at a time. In addition, the electrode patch is intended to be disposable, while the monitor recorder is a reusable component. Thus, each time that the electrode patch is replaced, a fresh battery is provided for the use of the monitor recorder.

Further, long-term electrocardiographic physiological monitoring over a period lasting up to several years in duration can be provided through a continuously-recording subcutaneous insertable cardiac monitor (ICM), such as one described in commonly-owned U.S. patent application Ser. No. 15/832,385, filed Dec. 5, 2017, abandoned, the disclosure of which is incorporated by reference. The sensing circuitry and the physical layout of the electrodes are specifically optimized to capture electrical signals from the propagation of low amplitude, relatively low frequency content cardiac action potentials, particularly the P-waves that are generated during atrial activation. In general, the ICM is intended to be implanted centrally and positioned axially and slightly to either the left or right of the sternal midline in the parasternal region of the chest.

In one embodiment, an insertable cardiac monitor (ICM) for use in performing long term electrocardiographic (ECG) monitoring is provided. The monitor includes; an implantable housing included of a biocompatible material that is suitable for implantation within a living body; at least one pair of ECG sensing electrodes provided on a ventral surface and on opposite ends of the implantable housing operatively placed to facilitate sensing in closest proximity to the low amplitude, low frequency content cardiac action potentials that are generated during atrial activation; and electronic circuitry provided within the housing assembly. The electronic circuitry includes an ECG front end circuit interfaced to a low-power microcontroller and configured to capture the cardiac action potentials sensed by the pair of ECG sensing electrodes which are output as ECG signals; the low power microcontroller operable to execute under modular micro program control as specified in firmware, the microcontroller operable to read samples of the ECG signals, buffer the samples of the ECG signals, compress the buffered samples of the ECG signals, buffer the compressed samples of the ECG signals, and write the buffered samples into a non-volatile flash memory; and the non-volatile memory electrically interfaced with the microcontroller and operable to store the written samples of the ECG signals.

Remote real-time streaming of ECG and other physiological data can occur based on a continuous communication connection between a cardiac monitor and a cloud server or between a home station and the cloud server. The cardiac monitor encrypts and transmits the data either directly to the cloud server or via a puck to the home station. Once received by the home station, the encrypted data is then transmitted to the cloud server, which then transmits the data to a remote physician via a computing device. Due to the continuous connection, the data transfer is in real-time, while the encryption provides a secure communication of the data.

An embodiment provides a system and method for remote ECG data streaming in real-time. ECG data is encrypted on a physiological monitor placed on a patient via a near-field communication chip on the physiological monitor. A continuous connection is established between the physiological monitor and a cloud-based server via a wireless transceiver on the physiological monitor. The encrypted ECG data is transmitted from the physiological monitor to the cloud-based server. The ECG data is then transmitted from the cloud-based server to a device associated with a medical professional in real-time.

Data can be communicated between an IMD, bedside monitor, and backend for data analysis, device updates, and charging. For example, the ICM can provide ECG data, logs, and component status to the backend via the bedside monitor, while the backend can provide ICM component firmware updates and initial charge parameters to the IMD via the bedside monitor. Additionally, the bedside monitor can communicate data directly to the backend without input from the 1 MB by providing logs for components of the bedside monitor and a status of the components. Conversely, the backend can provide firmware updates to the components of the bedside monitor.

The IMD can be charged using a puck that can be attached to or separate from the bedside monitor. Charging can be initialized by the 1 MB by providing charge parameters and updates to the charge parameters. During charging, data can also be communicated between the 1 MB and the bedside monitor via the charge waveforms, using Bluetooth, or via blanking, which interleaves charging and data transfer.

In a recovery mode, the bedside monitor can provide the IMD with debug commands, while the IMD provides error logs and bug responses to the bedside monitor. Also, upon starting up the bedside monitor, WiFi provisioning can be run to allow the user to set up the bedside monitor by connecting the bedside monitor to a user application via Bluetooth and receiving available networks for WiFi. Finally, the IMD can provide ECG data to the backend via a phone application, instead of via the bedside monitor.

An embodiment provides a method for data exchange and charging. An implantable medical device is monitored and charging of the implantable medical device is initiated by providing charge parameters to a bedside monitor. Communication is initiated between a puck associated with the bedside monitor and implantable medical device. The implantable medical device is charged using the charge parameters. Simultaneously with the charging, transfer of data between the implantable medical device and the bedside monitor is initiated.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

BRIEF DESCRIPTION OF THE DRAWINGS

FIGS. 12 and 13 are respectively top and bottom perspective views showing the ICM of FIG. 12.

DETAILED DESCRIPTION

Related Applications

This provisional patent application is related to in commonly-assigned U.S. Pat. No. 9,545,204, issued Jan. 17, 2017 to Bishay et al.; U.S. Pat. No. 9,730,593, issued Aug. 15, 2017 to Felix et al.; U.S. Pat. No. 9,717,432, issued Aug. 1, 2017 to Felix et al.; U.S. Pat. No. 9,775,536, issued Oct. 3, 2017 to Felix et al.; U.S. Pat. No. 9,433,380, issued Sep. 6, 2016 to Bishay et al.; U.S. Pat. No. 9,655,538, issued May 23, 2017 to Felix et al.; U.S. Pat. No. 9,364,155, issued Jun. 14, 2016 to Bardy et al.; U.S. Pat. No. 9,737,224, issued Aug. 22, 2017 to Bardy et al.; U.S. Pat. No. 9,433,367, issued Sep. 6, 2016 to Felix et al.; U.S. Pat. No. 9,700,227, issued Jul. 11, 2017 to Bishay et al.; U.S. Pat. No. 9,717,433, issued Aug. 1, 2017 to Felix et al.; U.S. Pat. No. 9,615,763, issued Apr. 11, 2017 to Felix et al.; U.S. Pat. No. 9,642,537, issued May 9, 2017 to Felix et al.; U.S. Pat. No. 9,408,545, issued Aug. 9, 2016 to Felix et al.; U.S. Pat. No. 9,655,537, issued May 23, 2017 to Bardy et al.; U.S. Pat. No. 10,165,946, issued Jan. 1, 2019 to Bardy et al.; U.S. Pat. No. 10,433,748, issued Oct. 8, 2019 to Bishay et al.; U.S. Pat. No. 10,667,711, issued Jun. 2, 2020 to Felix et al.; U.S. Pat. No. 9,619,660, issued Apr. 11, 2017 to Felix et al.; U.S. Pat. No. 10,463,269, issued Nov. 5, 2019 to Boleyn et al.; U.S. Pat. No. 9,408,551, issued Aug. 9, 2016 to Bardy et al.; U.S. Pat. No. 10,736,531, issued Aug. 11, 2020 to Bardy et al.; U.S. Pat. No. 10,736,529, issued Aug. 11, 2020 to Gust H. Bardy; U.S. Pat. No. 11,213,237, issued Jan. 4, 2022 to Bardy et al.; U.S. Patent Application Publication No. 2019/0099105, published Apr. 4, 2019 to Felix et al.; U.S. Pat. No. 10,624,551, issued Apr. 21, 2020 to Bardy et al.; U.S. Pat. No. 10,251,576, issued Apr. 9, 2019 to Bardy et al.; U.S. Pat. No. 9,345,414, issued May 24, 2016 to Bardy et al.; U.S. Pat. No. 10,433,751, issued Oct. 8, 2019 to Bardy et al.; U.S. Pat. No. 9,504,423, issued Nov. 29, 2016 to Bardy et al.; U.S. Patent Application Publication No. 2019/0167139, published Jun. 6, 2019 to Bardy et al.; U.S. Design Pat. No. D717955, issued Nov. 18, 2014 to Bishay et al.; U.S. Design Pat. No. D744659, issued Dec. 1, 2015 to Bishay et al.; U.S. Design Pat. No. D838370, issued Jan. 15, 2019 to Bardy et al.; U.S. Design Pat. No. D801528, issued Oct. 31, 2017 to Bardy et al.; U.S. Design Pat. No. D766447, issued Sep. 13, 2016 to Bishay et al.; U.S. Design Pat. No. D793566, issued Aug. 1, 2017 to Bishay et al.; U.S. Design Pat. No. D831833, issued Oct. 23, 2018 to Bishay et al.; U.S. Design Pat. No. D892,340, issued Aug. 4, 2020 to Bishay et al., and Provisional Patent Application No. 62/870,506, entitled: "Subcutaneous P-Wave Centric Cardiac Monitor With Energy Harvesting Capabilities," filed Jul. 3, 2019, pending, the disclosures of which are incorporated by reference.

Overview

Figure 1:
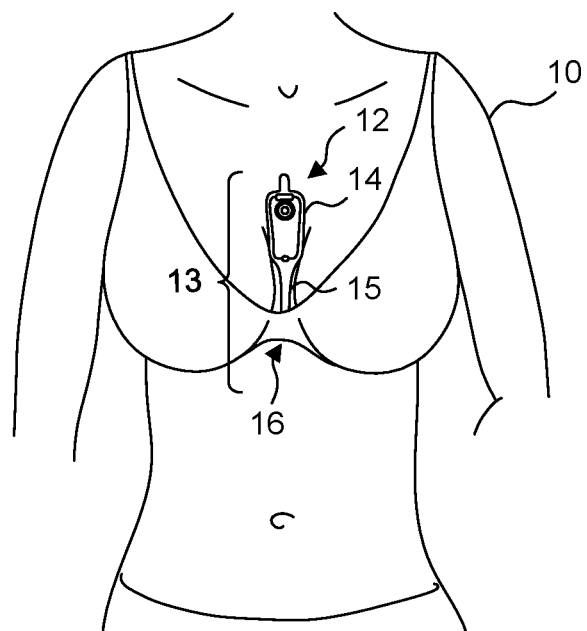
FIGS. 1 and 2 are diagrams showing, by way of examples, an extended wear electrocardiography and physiological sensor monitor, including a monitor recorder in accordance with one embodiment, respectively fitted to the sternal region of a female patient and a male patient.
Figure 2:
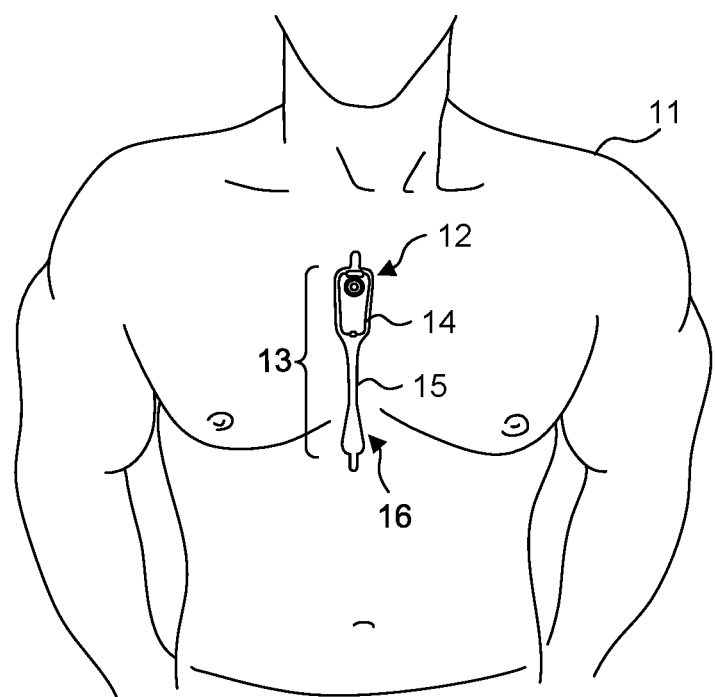

Physiological monitoring can be provided through a wearable monitor that includes two components, a flexible extended wear electrode patch and a removable reusable monitor recorder. FIGS. 1 and 2 are diagrams showing, by way of examples, an extended wear electrocardiography and physiological sensor monitor 12, including a monitor recorder 14 in accordance with one embodiment, respectively fitted to the sternal region of a female patient 10 and a male patient 11. The wearable monitor 12 sits centrally (in the midline) on the patient's chest along the sternum 13 oriented top-to-bottom with the monitor recorder 14 preferably situated towards the patient's head. In a further embodiment, the orientation of the wearable monitor 12 can be corrected post-monitoring, as further described infra. The electrode patch 15 is shaped to fit comfortably and conformal to the contours of the patient's chest approximately centered on the sternal midline 16 (or immediately to either side of the sternum 13). The distal end of the electrode patch 15 extends towards the Xiphoid process and, depending upon the patient's build, may straddle the region over the Xiphoid process. The proximal end of the electrode patch 15, located under the monitor recorder 14, is below the manubrium and, depending upon patient's build, may straddle the region over the manubrium.

The placement of the wearable monitor 12 in a location at the sternal midline 16 (or immediately to either side of the sternum 13) significantly improves the ability of the wearable monitor 12 to cutaneously sense cardiac electric signals, particularly the P-wave (or atrial activity) and, to a lesser extent, the QRS interval signals in the ECG waveforms that indicate ventricular activity. The sternum 13 overlies the right atrium of the heart and the placement of the wearable monitor 12 in the region of the sternal midline 13 puts the ECG electrodes of the electrode patch 15 in a location better adapted to sensing and recording P-wave signals than other placement locations, say, the upper left pectoral region. In addition, placing the lower or inferior pole (ECG electrode) of the electrode patch 15 over (or near) the Xiphoid process facilitates sensing of right ventricular activity and provides superior recordation of the QRS interval.

Figure 3:
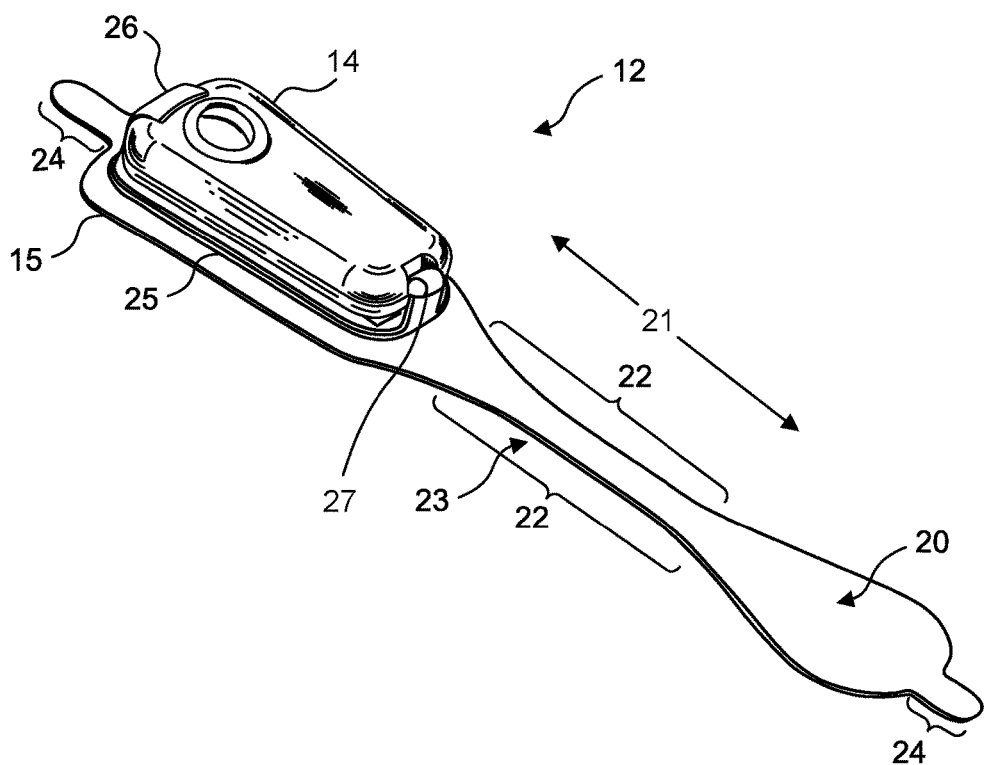
FIG. 3 is a perspective view showing an extended wear electrode patch with a monitor recorder in accordance with one embodiment inserted.

During use, the electrode patch 15 is first adhesed to the skin along the sternal midline 16 (or immediately to either side of the sternum 13). A monitor recorder 14 is then snapped into place on the electrode patch 15 to initiate ECG monitoring. FIG. 3 is a perspective view showing an extended wear electrode patch 15 with a monitor recorder 14 in accordance with one embodiment inserted. The body of the electrode patch 15 is preferably constructed using a flexible backing 20 formed as an elongated strip 21 of wrap knit or similar stretchable material with a narrow longitudinal mid-section 23 evenly tapering inward from both sides. A pair of cut-outs 22 between the distal and proximal ends of the electrode patch 15 create a narrow longitudinal midsection 23 or "isthmus" and defines an elongated "hourglass"-like shape, when viewed from above.

The electrode patch 15 incorporates features that significantly improve wearability, performance, and patient comfort throughout an extended monitoring period. During wear, the electrode patch 15 is susceptible to pushing, pulling, and torquing movements, including compressional and torsional forces when the patient bends forward, and tensile and torsional forces when the patient leans backwards. To counter these stress forces, the electrode patch 15 incorporates strain and crimp reliefs, such as described in commonly-assigned U.S. patent, entitled "Extended Wear Electrocardiography Patch," U.S. Pat. No. 9,545,204, issued on Jan. 17, 2017, the disclosure of which is incorporated by reference. In addition, the cut-outs 22 and longitudinal midsection 23 help minimize interference with and discomfort to breast tissue, particularly in women (and gynecomastic men). The cut-outs 22 and longitudinal midsection 23 further allow better conformity of the electrode patch 15 to sternal bowing and to the narrow isthmus of flat skin that can occur along the bottom of the intermammary cleft between the breasts, especially in buxom women. The cut-outs 22 and longitudinal midsection 23 help the electrode patch 15 fit nicely between a pair of female breasts in the intermammary cleft. Still other shapes, cut-outs and conformities to the electrode patch 15 are possible.

The monitor recorder 14 removably and reusably snaps into an electrically non-conductive receptacle 25 during use. The monitor recorder 14 contains electronic circuitry for recording and storing the patient's electrocardiography as sensed via a pair of ECG electrodes provided on the electrode patch 15, as further described infra beginning with reference to FIG. 8. The non-conductive receptacle 25 is provided on the top surface of the flexible backing 20 with a retention catch 26 and tension clip 27 molded into the non-conductive receptacle 25 to conformably receive and securely hold the monitor recorder 14 in place.

Figure 4:
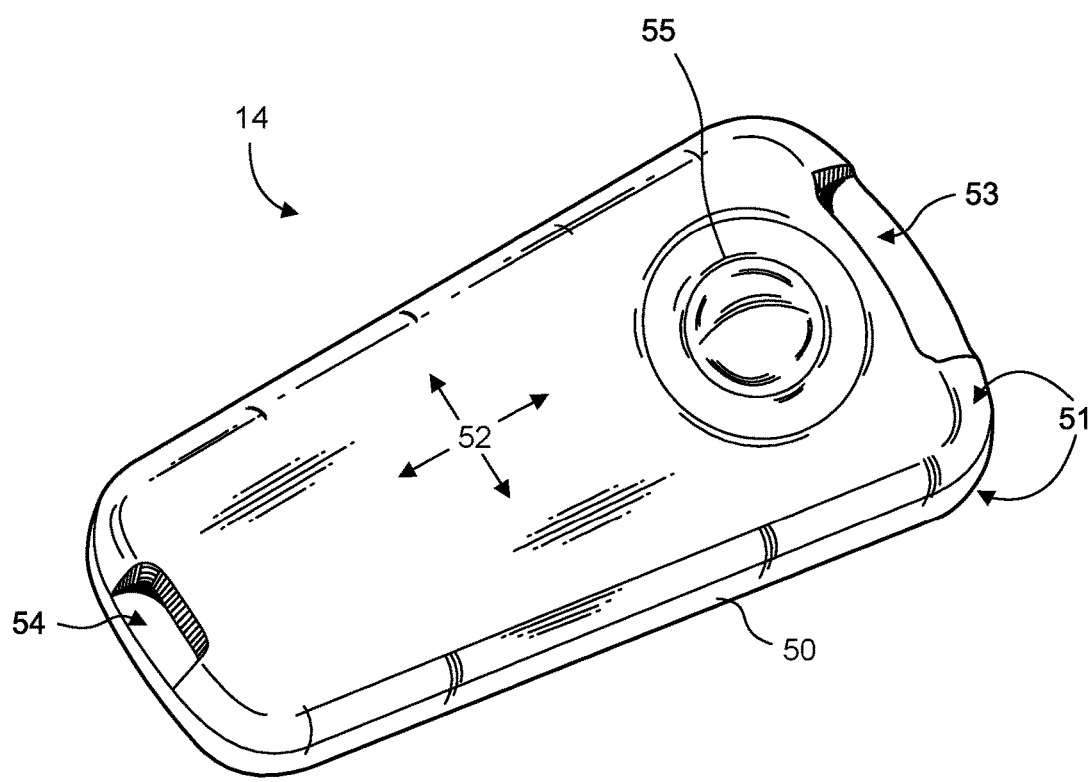
FIG. 4 is a perspective view showing the monitor recorder of FIG. 3.

The monitor recorder 14 includes a sealed housing that snaps into place in the non-conductive receptacle 25. FIG. 4 is a perspective view showing the monitor recorder 14 of FIG. 3. The sealed housing 50 of the monitor recorder 14 intentionally has a rounded isosceles trapezoidal-like shape 52, when viewed from above, such as described in commonly-assigned U.S. Design patent, entitled "Electrocardiography Monitor," No. D717955, issued on Nov. 18, 2014, the disclosure of which is incorporated by reference. The edges 51 along the top and bottom surfaces are rounded for patient comfort. The sealed housing 50 is approximately 47 mm long, 23 mm wide at the widest point, and 7 mm high, excluding a patient-operable tactile-feedback button 55. The sealed housing 50 can be molded out of polycarbonate, ABS, or an alloy of those two materials. The button 55 is waterproof and the button's top outer surface is molded silicon rubber or similar soft pliable material. A retention detent 53 and tension detent 54 are molded along the edges of the top surface of the housing 50 to respectively engage the retention catch 26 and the tension clip 27 molded into non-conductive receptacle 25. Other shapes, features, and conformities of the sealed housing 50 are possible.

The electrode patch 15 is intended to be disposable. The monitor recorder 14, however, is reusable and can be transferred to successive electrode patches 15 to ensure continuity of monitoring. The placement of the wearable monitor 12 in a location at the sternal midline 16 (or immediately to either side of the sternum 13) benefits long-term extended wear by removing the requirement that ECG electrodes be continually placed in the same spots on the skin throughout the monitoring period. Instead, the patient is free to place an electrode patch 15 anywhere within the general region of the sternum 13.

As a result, at any point during ECG monitoring, the patient's skin is able to recover from the wearing of an electrode patch 15, which increases patient comfort and satisfaction, while the monitor recorder 14 ensures ECG monitoring continuity with minimal effort. A monitor recorder 14 is merely unsnapped from a worn out electrode patch 15, the worn out electrode patch 15 is removed from the skin, a new electrode patch 15 is adhered to the skin, possibly in a new spot immediately adjacent to the earlier location, and the same monitor recorder 14 is snapped into the new electrode patch 15 to reinitiate and continue the ECG monitoring.

Figure 5:
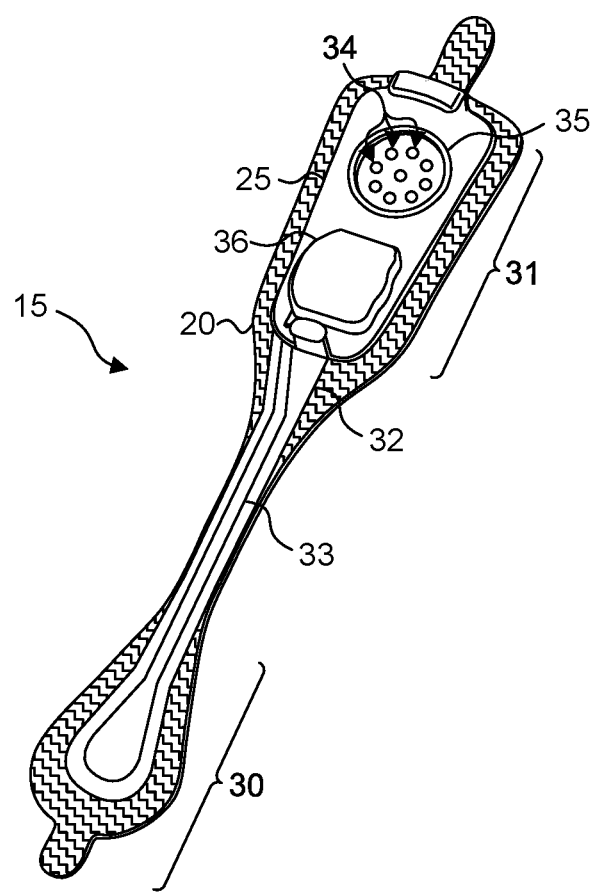
FIG. 5 is a perspective view showing the extended wear electrode patch of FIG. 3 without a monitor recorder inserted.

During use, the electrode patch 15 is first adhered to the skin in the sternal region. FIG. 5 is a perspective view showing the extended wear electrode patch 15 of FIG. 3 without a monitor recorder 14 inserted. A flexible circuit 32 is adhered to each end of the flexible backing 20. A distal circuit trace 33 and a proximal circuit trace (not shown) electrically couple ECG electrodes (not shown) to a pair of electrical pads 34. The electrical pads 34 are provided within a moisture-resistant seal 35 formed on the bottom surface of the non-conductive receptacle 25. When the monitor recorder 14 is securely received into the non-conductive receptacle 25, that is, snapped into place, the electrical pads 34 interface to electrical contacts (not shown) protruding from the bottom surface of the monitor recorder 14, and the moisture-resistant seal 35 enables the monitor recorder 14 to be worn at all times, even during bathing or other activities that could expose the monitor recorder 14 to moisture.

In addition, a battery compartment 36 is formed on the bottom surface of the non-conductive receptacle 25, and a pair of battery leads (not shown) electrically interface the battery to another pair of the electrical pads 34. The battery contained within the battery compartment 35 can be replaceable, rechargeable or disposable.

Figure 6:
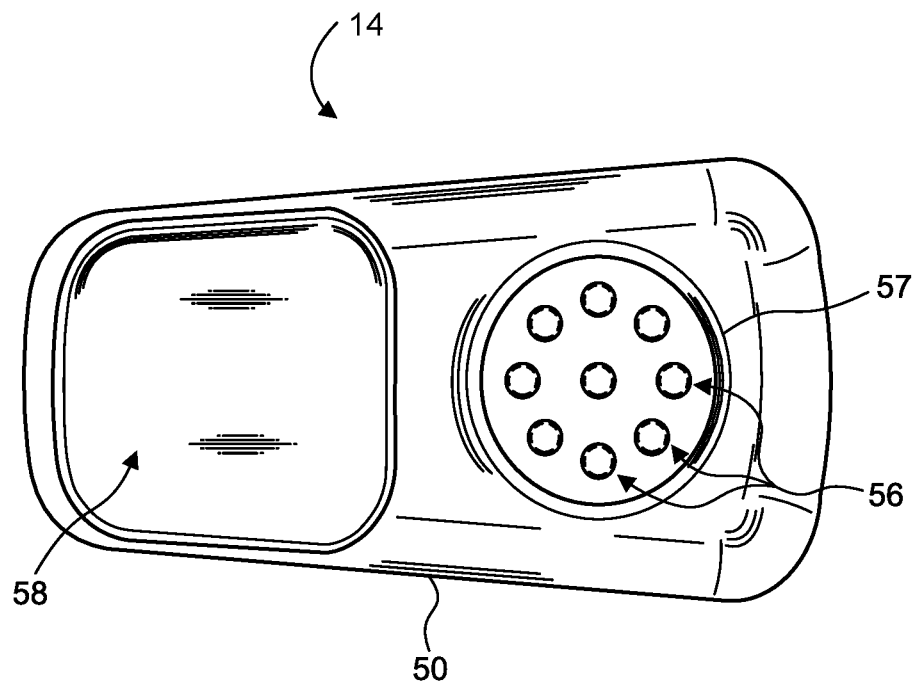
FIG. 6 is a bottom plan view of the monitor recorder of FIG. 3.

The monitor recorder 14 draws power externally from the battery provided in the non-conductive receptacle 25, thereby uniquely obviating the need for the monitor recorder 14 to carry a dedicated power source. FIG. 6 is a bottom plan view of the monitor recorder 14 of FIG. 3. A cavity 58 is formed on the bottom surface of the sealed housing 50 to accommodate the upward projection of the battery compartment 36 from the bottom surface of the non-conductive receptacle 25, when the monitor recorder 14 is secured in place on the non-conductive receptacle 25. A set of electrical contacts 56 protrude from the bottom surface of the sealed housing 50 and are arranged in alignment with the electrical pads 34 provided on the bottom surface of the non-conductive receptacle 25 to establish electrical connections between the electrode patch 15 and the monitor recorder 14. In addition, a seal coupling 57 circumferentially surrounds the set of electrical contacts 56 and securely mates with the moisture-resistant seal 35 formed on the bottom surface of the non-conductive receptacle 25.

The placement of the flexible backing 20 on the sternal midline 16 (or immediately to either side of the sternum 13) also helps to minimize the side-to-side movement of the wearable monitor 12 in the left- and right-handed directions during wear. To counter the dislodgment of the flexible backing 20 due to compressional and torsional forces, a layer of non-irritating adhesive, such as hydrocolloid, is provided at least partially on the underside, or contact, surface of the flexible backing 20, but only on the distal end 30 and the proximal end 31. As a result, the underside, or contact surface of the longitudinal midsection 23 does not have an adhesive layer and remains free to move relative to the skin. Thus, the longitudinal midsection 23 forms a crimp relief that respectively facilitates compression and twisting of the flexible backing 20 in response to compressional and torsional forces. Other forms of flexible backing crimp reliefs are possible.

Figure 7:
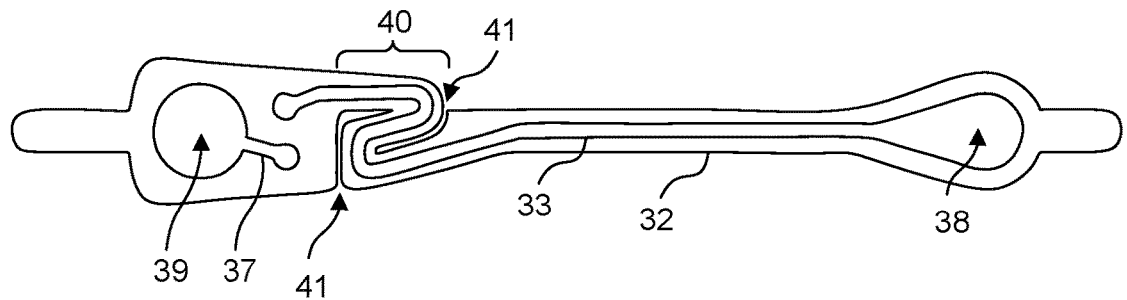
FIG. 7 is a top view showing the flexible circuit of the extended wear electrode patch of FIG. 3 when mounted above the flexible backing.

Unlike the flexible backing 20, the flexible circuit 32 is only able to bend and cannot stretch in a planar direction. The flexible circuit 32 can be provided either above or below the flexible backing 20. FIG. 7 is a top view showing the flexible circuit 32 of the extended wear electrode patch 15 of FIG. 3 when mounted above the flexible backing 20. A distal ECG electrode 38 and proximal ECG electrode 39 are respectively coupled to the distal and proximal ends of the flexible circuit 32. A strain relief 40 is defined in the flexible circuit 32 at a location that is partially underneath the battery compartment 36 when the flexible circuit 32 is affixed to the flexible backing 20. The strain relief 40 is laterally extendable to counter dislodgment of the ECG electrodes 38, 39 due to tensile and torsional forces. A pair of strain relief cutouts 41 partially extend transversely from each opposite side of the flexible circuit 32 and continue longitudinally towards each other to define in 'S'-shaped pattern, when viewed from above. The strain relief respectively facilitates longitudinal extension and twisting of the flexible circuit 32 in response to tensile and torsional forces. Other forms of circuit board strain relief are possible.

Figure 8:
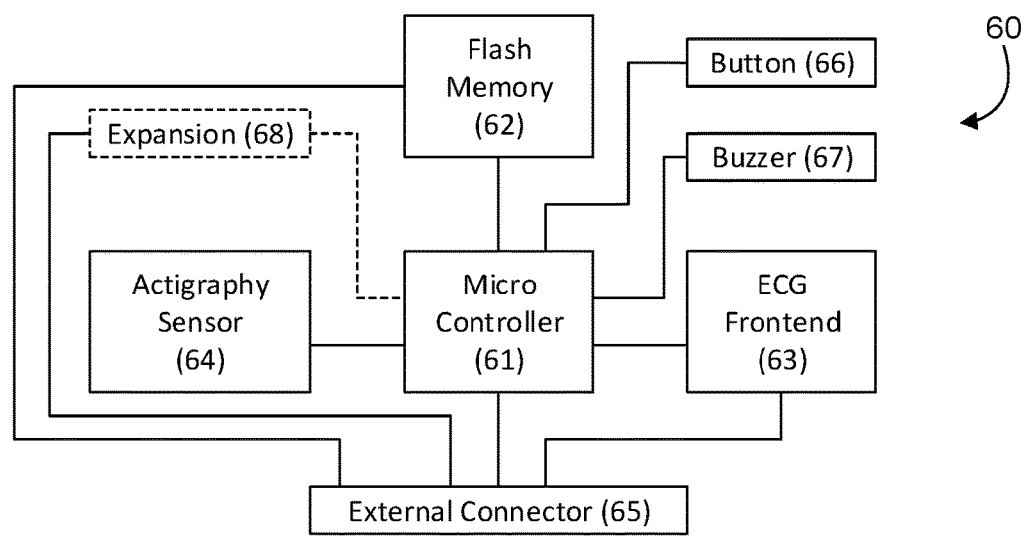
FIG. 8 is a functional block diagram showing the component architecture of the circuitry of the monitor recorder of FIG. 3.

ECG monitoring and other functions performed by the monitor recorder 14 are provided through a micro controlled architecture. FIG. 8 is a functional block diagram showing the component architecture of the circuitry 60 of the monitor recorder 14 of FIG. 3. The circuitry 60 is externally powered through a battery provided in the non-conductive receptacle 25 (shown in FIG. 5). Both power and raw ECG signals, which originate in the pair of ECG electrodes 38, 39 (shown in FIG. 7) on the distal and proximal ends of the electrode patch 15, are received through an external connector 65 that mates with a corresponding physical connector on the electrode patch 15. The external connector 65 includes the set of electrical contacts 56 that protrude from the bottom surface of the sealed housing 50 and which physically and electrically interface with the set of pads 34 provided on the bottom surface of the non-conductive receptacle 25. The external connector includes electrical contacts 56 for data download, microcontroller communications, power, analog inputs, and a peripheral expansion port. The arrangement of the pins on the electrical connector 65 of the monitor recorder 14 and the device into which the monitor recorder 14 is attached, whether an electrode patch 15 or download station (not shown), follow the same electrical pin assignment convention to facilitate interoperability. The external connector 65 also serves as a physical interface to a download station that permits the retrieval of stored ECG monitoring data, communication with the monitor recorder 14, and performance of other functions. Operation of the circuitry 60 of the monitor recorder 14 is managed by a microcontroller 61. The micro-controller 61 includes a program memory unit containing internal flash memory that is readable and writeable. The internal flash memory can also be programmed externally. The micro-controller 61 draws power externally from the battery provided on the electrode patch 15 via a pair of the electrical contacts 56. The microcontroller 61 connects to the ECG front end circuit 63 that measures raw cutaneous electrical signals and generates an analog ECG signal representative of the electrical activity of the patient's heart over time.

The circuitry 60 of the monitor recorder 14 also includes a flash memory 62, which the micro-controller 61 uses for storing ECG monitoring data and other physiology and information. The flash memory 62 also draws power externally from the battery provided on the electrode patch 15 via a pair of the electrical contacts 56. Data is stored in a serial flash memory circuit, which supports read, erase and program operations over a communications bus. The flash memory 62 enables the microcontroller 61 to store digitized ECG data. The communications bus further enables the flash memory 62 to be directly accessed externally over the external connector 65 when the monitor recorder 14 is interfaced to a download station.

The circuitry 60 of the monitor recorder 14 further includes an actigraphy sensor 64 implemented as a 3-axis accelerometer. The accelerometer may be configured to generate interrupt signals to the microcontroller 61 by independent initial wake up and free fall events, as well as by device position. In addition, the actigraphy provided by the accelerometer can be used during post-monitoring analysis to correct the orientation of the monitor recorder 14 if, for instance, the monitor recorder 14 has been inadvertently installed upside down, that is, with the monitor recorder 14 oriented on the electrode patch 15 towards the patient's feet, as well as for other event occurrence analyses.

The microcontroller 61 includes an expansion port that also utilizes the communications bus. External devices, separately drawing power externally from the battery provided on the electrode patch 15 or other source, can interface to the microcontroller 61 over the expansion port in half duplex mode. For instance, an external physiology sensor can be provided as part of the circuitry 60 of the monitor recorder 14, or can be provided on the electrode patch 15 with communication with the micro-controller 61 provided over one of the electrical contacts 56. The physiology sensor can include an $SpO_2$ sensor, blood pressure sensor, temperature sensor, respiratory rate sensor, glucose sensor, airflow sensor, volumetric pressure sensing, or other types of sensor or telemetric input sources. In a further embodiment, a wireless interface for interfacing with other wearable (or implantable) physiology monitors, as well as data offload and programming, can be provided as part of the circuitry 60 of the monitor recorder 14, or can be provided on the electrode patch 15 with communication with the micro-controller 61 provided over one of the electrical contacts 56.

Finally, the circuitry 60 of the monitor recorder 14 includes patient-interfaceable components, including a tactile feedback button 66, which a patient can press to mark events or to perform other functions, and a buzzer 67, such as a speaker, magnetic resonator or piezoelectric buzzer. The buzzer 67 can be used by the microcontroller 61 to output feedback to a patient such as to confirm power up and initiation of ECG monitoring. Still other components as part of the circuitry 60 of the monitor recorder 14 are possible.

Figure 9:
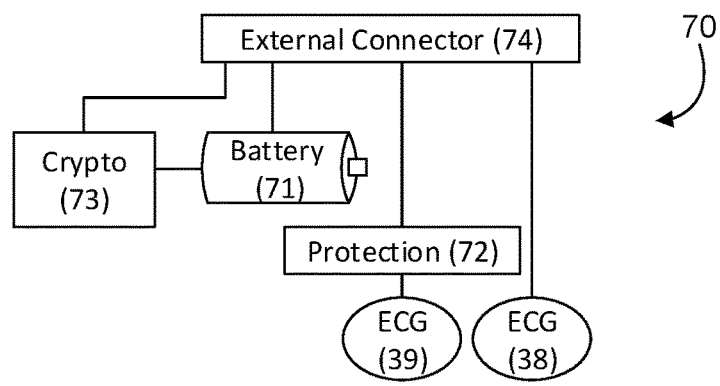
FIG. 9 is a functional block diagram showing the circuitry of the extended wear electrode patch of FIG. 3.

While the monitor recorder 14 operates under micro control, most of the electrical components of the electrode patch 15 operate passively. FIG. 9 is a functional block diagram showing the circuitry 70 of the extended wear electrode patch 15 of FIG. 3. The circuitry 70 of the electrode patch 15 is electrically coupled with the circuitry 60 of the monitor recorder 14 through an external connector 74. The external connector 74 is terminated through the set of pads 34 provided on the bottom of the non-conductive receptacle 25, which electrically mate to corresponding electrical contacts 56 protruding from the bottom surface of the sealed housing 50 to electrically interface the monitor recorder 14 to the electrode patch 15.

The circuitry 70 of the electrode patch 15 performs three primary functions. First, a battery 71 is provided in a battery compartment formed on the bottom surface of the non-conductive receptacle 25. The battery 71 is electrically interfaced to the circuitry 60 of the monitor recorder 14 as a source of external power. The unique provisioning of the battery 71 on the electrode patch 15 provides several advantages. First, the locating of the battery 71 physically on the electrode patch 15 lowers the center of gravity of the overall wearable monitor 12 and thereby helps to minimize shear forces and the effects of movements of the patient and clothing. Moreover, the housing 50 of the monitor recorder 14 is sealed against moisture and providing power externally avoids having to either periodically open the housing 50 for the battery replacement, which also creates the potential for moisture intrusion and human error, or to recharge the battery, which can potentially take the monitor recorder 14 off line for hours at a time. In addition, the electrode patch 15 is intended to be disposable, while the monitor recorder 14 is a reusable component. Each time that the electrode patch 15 is replaced, a fresh battery is provided for the use of the monitor recorder 14, which enhances ECG monitoring performance quality and duration of use. Finally, the architecture of the monitor recorder 14 is open, in that other physiology sensors or components can be added by virtue of the expansion port of the microcontroller 61. Requiring those additional sensors or components to draw power from a source external to the monitor recorder 14 keeps power considerations independent of the monitor recorder 14. Thus, a battery of higher capacity could be introduced when needed to support the additional sensors or components without effecting the monitor recorders circuitry 60.

Second, the pair of ECG electrodes 38, 39 respectively provided on the distal and proximal ends of the flexible circuit 32 are electrically coupled to the set of pads 34 provided on the bottom of the non-conductive receptacle 25 by way of their respective circuit traces 33, 37. The signal ECG electrode 39 includes a protection circuit 72, which is an inline resistor that protects the patient from excessive leakage current.

Last, in a further embodiment, the circuitry 70 of the electrode patch 15 includes a cryptographic circuit 73 to authenticate an electrode patch 15 for use with a monitor recorder 14. The cryptographic circuit 73 includes a device capable of secure authentication and validation. The cryptographic device 73 ensures that only genuine, non-expired, safe, and authenticated electrode patches 15 are permitted to provide monitoring data to a monitor recorder 14.

Figure 10:
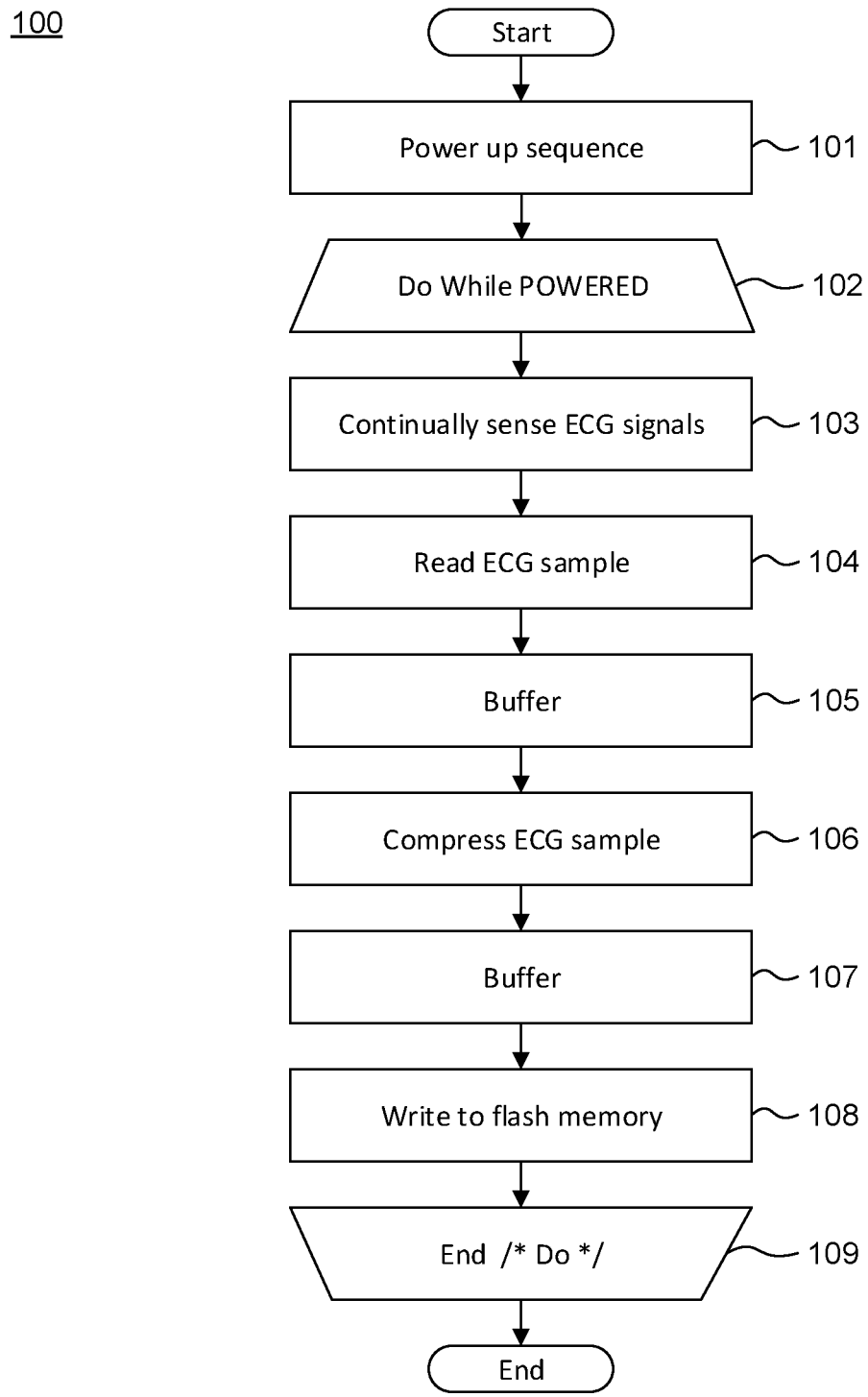
FIG. 10 is a flow diagram showing a monitor recorder-implemented method for monitoring ECG data for use in the monitor recorder of FIG. 3.

The monitor recorder 14 continuously monitors the patient's heart rate and physiology. FIG. 10 is a flow diagram showing a monitor recorder-implemented method 100 for monitoring ECG data for use in the monitor recorder 14 of FIG. 3. Initially, upon being connected to the set of pads 34 provided with the non-conductive receptacle 25 when the monitor recorder 14 is snapped into place, the microcontroller 61 executes a power up sequence (step 101). During the power up sequence, the voltage of the battery 71 is checked, the state of the flash memory 62 is confirmed, both in terms of operability check and available capacity, and microcontroller operation is diagnostically confirmed. In a further embodiment, an authentication procedure between the microcontroller 61 and the electrode patch 15 are also performed.

Figure 11:
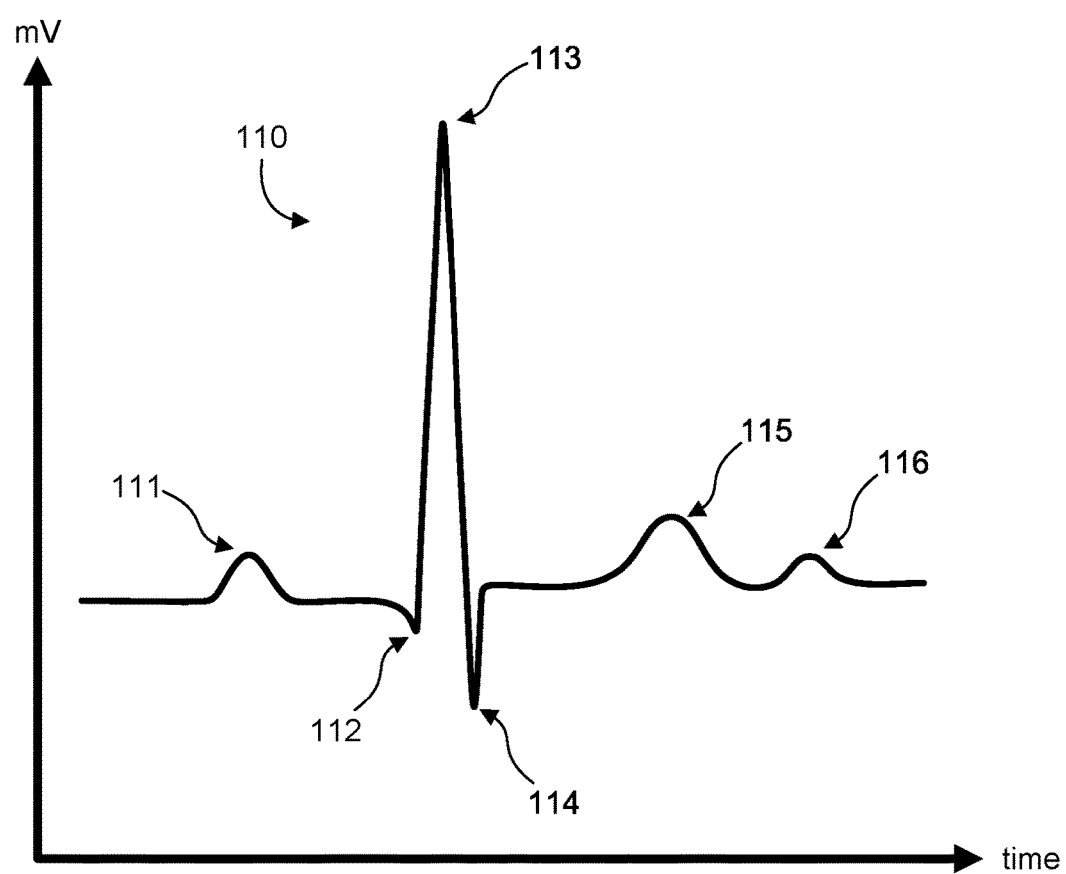
FIG. 11 is a graph showing, by way of example, a typical ECG waveform.

Following satisfactory completion of the power up sequence, an iterative processing loop (steps 102-109) is continually executed by the microcontroller 61. During each iteration (step 102) of the processing loop, the ECG frontend 63 (shown in FIG. 8) continually senses the cutaneous ECG electrical signals (step 103) via the ECG electrodes 38, 29 and is optimized to maintain the integrity of the P-wave. A sample of the ECG signal is read (step 104) by the microcontroller 61 by sampling the analog ECG signal output front end 63. FIG. 11 is a graph showing, by way of example, a typical ECG waveform 110. The x-axis represents time in approximate units of tenths of a second. The y-axis represents cutaneous electrical signal strength in approximate units of millivolts. The P-wave 111 has a smooth, normally upward, that is, positive, waveform that indicates atrial depolarization. The QRS complex usually begins with the downward deflection of a Q wave 112, followed by a larger upward deflection of an R-wave 113, and terminated with a downward waveform of the S wave 114, collectively representative of ventricular depolarization. The T wave 115 is normally a modest upward waveform, representative of ventricular depolarization, while the U wave 116, often not directly observable, indicates the recovery period of the Purkinje conduction fibers.

Sampling of the R-to-R interval enables heart rate information derivation. For instance, the R-to-R interval represents the ventricular rate and rhythm, while the P-to-P interval represents the atrial rate and rhythm. Importantly, the PR interval is indicative of atrioventricular (AV) conduction time and abnormalities in the PR interval can reveal underlying heart disorders, thus representing another reason why the P-wave quality achievable by the extended wear ambulatory electrocardiography and physiological sensor monitor described herein is medically unique and important. The long-term observation of these ECG indicia, as provided through extended wear of the wearable monitor 12, provides valuable insights to the patient's cardiac function and overall well-being.

Each sampled ECG signal, in quantized and digitized form, is temporarily staged in buffer (step 105), pending compression preparatory to storage in the flash memory 62 (step 106). Following compression, the compressed ECG digitized sample is again buffered (step 107), then written to the flash memory 62 (step 108) using the communications bus. Processing continues (step 109), so long as the monitoring recorder 14 remains connected to the electrode patch 15 (and storage space remains available in the flash memory 62), after which the processing loop is exited and execution terminates. Still other operations and steps are possible.

Figure 12:
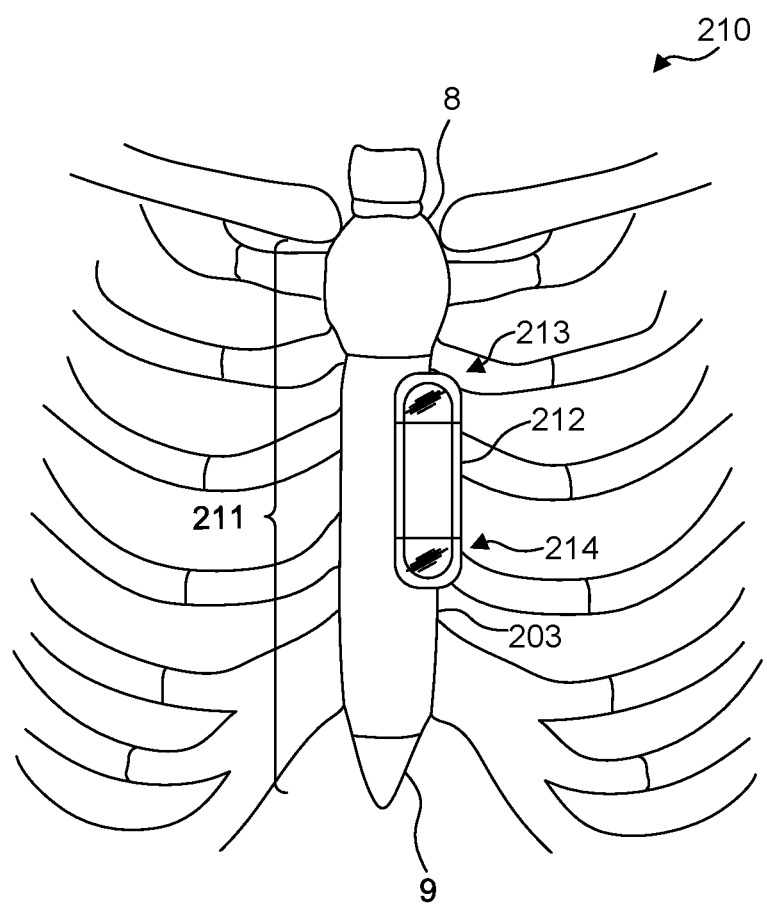
FIG. 12 is a diagram showing, by way of example, a subcutaneous P-wave centric insertable cardiac monitor (ICM) for long term electrocardiographic monitoring in accordance with one embodiment.

In a further embodiment, physiological monitoring and data collection, such as per the method 100 described above with reference to FIG. 10, can also be implemented by a continuously-recording subcutaneous insertable cardiac monitor (ICM), such as one described in commonly-owned U.S. patent application Ser. No. 15/832,385, filed Dec. 5, 2017, abandoned, the disclosure of which is incorporated by reference. The ICM can be used for conducting a long-term electrocardiogram and physiological monitoring over a period lasting up to several years in duration. FIG. 12 is a diagram showing, by way of example, a subcutaneous P-wave centric ICM 212 for long term electrocardiographic monitoring in accordance with one embodiment. The ICM 212 is implanted in the parasternal region 211 of a patient 10. The sensing circuitry and components, compression algorithms, and the physical layout of the electrodes are specifically optimized to capture electrical signals from the propagation of low amplitude, relatively low frequency content cardiac action potentials, particularly the P-waves generated during atrial activation. The position and placement of the ICM 212 coupled to engineering considerations that optimize the ICM's sensing circuitry, discussed infra, aid in demonstrating the P-wave clearly.

Implantation of a P-wave centric ICM 212 in the proper subcutaneous site facilitates the recording of high quality ECG data with a good delineation of the P-wave. In general, the ICM 212 is intended to be implanted anteriorly and be positioned axially and slightly to either the right or left of the sternal midline in the parasternal region 211 of the chest, or if sufficient subcutaneous fat exists, directly over the sternum. Optimally, the ICM 212 is implanted in a location left parasternally to bridge the left atrial appendage. However, either location to the right or left of the sternal midline is acceptable; placement of the device, if possible, should bridge the vertical height of the heart, which lies underneath the sternum 203, thereby placing the ICM 212 in close proximity to the anterior right atrium and the left atrial appendage that lie immediately beneath.

The ICM 212 is shaped to fit comfortably within the body under the skin and to conform to the contours of the patient's parasternal region 211 when implanted immediately to either side of the sternum 203, but could be implanted in other locations of the body. In most adults, the proximal end 213 of the ICM 212 is generally positioned below the manubrium 8 but, depending upon patient's vertical build, the ICM 212 may actually straddle the region over the manubrium 8. The distal end 214 of the ICM 212 generally extends towards the xiphoid process 9 and lower sternum but, depending upon the patient's build, may actually straddle the region over or under the xiphoid process 9, lower sternum and upper abdomen.

Although internal tissues, body structures, and tissue boundaries can adversely affect the current strength and signal fidelity of all body surface potentials, subsurface low amplitude cardiac action potentials, particularly P-wave signals with a normative amplitude of less than 0.25 millivolts (mV) and a normative duration of less than 120 milliseconds (ms), are most apt to be negatively impacted by these factors. The atria, which generate the P wave, are mostly located posteriorly within the thoracic cavity (with the exception of the anterior right atrium, right atrial appendage and left atrial appendage). The majority of the left atrium constitutes the portion of the heart furthest away from the surface of the skin on the chest and harbors the atrial tissue most likely to be the source of serious arrhythmias, like atrial fibrillation. Conversely, the ventricles, which generate larger amplitude signals, are located anteriorly as in the case of the anterior right ventricle and most of the anterior left ventricle situated relatively close to the skin surface of the central and left anterior chest. These factors, together with larger size and more powerful impulse generation from the ventricles, contribute to the relatively larger amplitudes of ventricular waveforms.

Nevertheless, as explained supra, both the P-wave and the R-wave are required for the physician to make a proper rhythm diagnosis from the dozens of arrhythmias that can occur. Yet, the quality of P-waves is more susceptible to weakening from distance and the intervening tissues and structures and from signal attenuation and signal processing than the high voltage waveforms associated with ventricular activation. The added value of avoiding further signal attenuation resulting from dermal impedance makes a subcutaneous P-wave centric ICM even more likely to match, or even outperform dermal ambulatory monitors designed to analogous engineering considerations and using similar sensing circuitry and components, compression algorithms, and physical layout of electrodes, such as described in U.S. Pat. No. 9,545,204, issued January 217, 20217 to Bishay et al.; U.S. Pat. No. 9,730,593, issued Aug. 15, 20217 to Felix et al.; U.S. Pat. No. 9,700,227, issued Jul. 11, 20217 to Bishay et al.; U.S. Pat. No. 9,7217,433, issued Aug. 1, 20217 to Felix et al.; and U.S. Pat. No. 9,615,763, issued Apr. 11, 20217 to Felix et al., the disclosures of which are incorporated by reference.

The ICM 212 can be implanted in the patient's chest using, for instance, a minimally invasive subcutaneous implantation instrument or other suitable surgical implement. The ICM 212 is positioned slightly to the right or left of midline, covering the center third of the chest, roughly between the second and sixth ribs, approximately spanning between the level of the manubrium 8 and the level of the xiphoid process 9 on the inferior border of the sternum 203, depending upon the vertical build of the patient 210.

During monitoring, the amplitude and strength of action potentials sensed by an ECG devices, including dermal ECG monitors and ICMs, can be affected to varying degrees by cardiac, cellular, extracellular, vector of current flow, and physical factors, like obesity, dermatitis, lung disease, large breasts, and high impedance skin, as can occur in dark-skinned individuals. Performing ECG sensing subcutaneously in the parasternal region 211 significantly improves the ability of the ICM 212 to counter some of the effects of these factors, particularly high skin impedance and impedance from subcutaneous fat. Thus, the ICM 212 exhibits superior performance when compared to conventional dermal ECG monitors to existing implantable loop recorders, ICMs, and other forms of implantable monitoring devices by virtue of its engineering and proven P-wave documentation above the skin, as discussed in W. M. Smith et al., "Comparison of diagnostic value using a small, single channel, P-wave centric sternal ECG monitoring patch with a standard 3-lead Holter system over 24 hours," Am. Heart J., March 20217; 2185:67-73, the disclosure of which is incorporated by reference.

Moreover, the sternal midline implantation location in the parasternal region 211 allows the ICM's electrodes to record an ECG of optimal signal quality from a location immediately above the strongest signal-generating aspects of the atrial. Signal quality is improved further in part because cardiac action potential propagation travels simultaneously along a north-to-south and right-to-left vector, beginning high in the right atrium and ultimately ending in the posterior and lateral region of the left ventricle. Cardiac depolarization originates high in the right atrium in the SA node before concurrently spreading leftward towards the left atrium and inferiorly towards the atrioventricular (AV) node. On the proximal end 213, the ECG electrodes of the ICM 212 are subcutaneously positioned with the upper or superior pole (ECG electrode) slightly to the right or left of the sternal midline in the region of the manubrium 8 and, on the distal end 214, the lower or inferior pole (ECG electrode) is similarly situated slightly to the right or left of the sternal midline in the region of the xiphoid process 9 and lower sternum 203. The ECG electrodes of the ICM 212 are placed primarily in a north-to-south orientation along the sternum 203 that corresponds to the north-to-south waveform vector exhibited during atrial activation. This orientation corresponds to the aVF lead used in a conventional 12-lead ECG that is used to sense positive or upright P-waves. In addition, the electrode spacing and the electrodes' shapes and surface areas mimic the electrodes used in the ICM's dermal cousin, designed as part of the optimal P-wave sensing electrode configuration, such as provided with the dermal ambulatory monitors cited supra.

Figure 13:
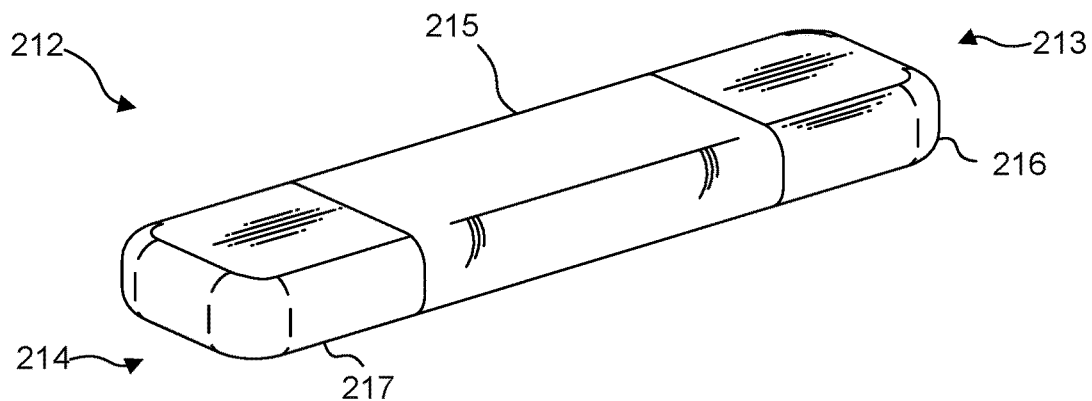
Figure 14:
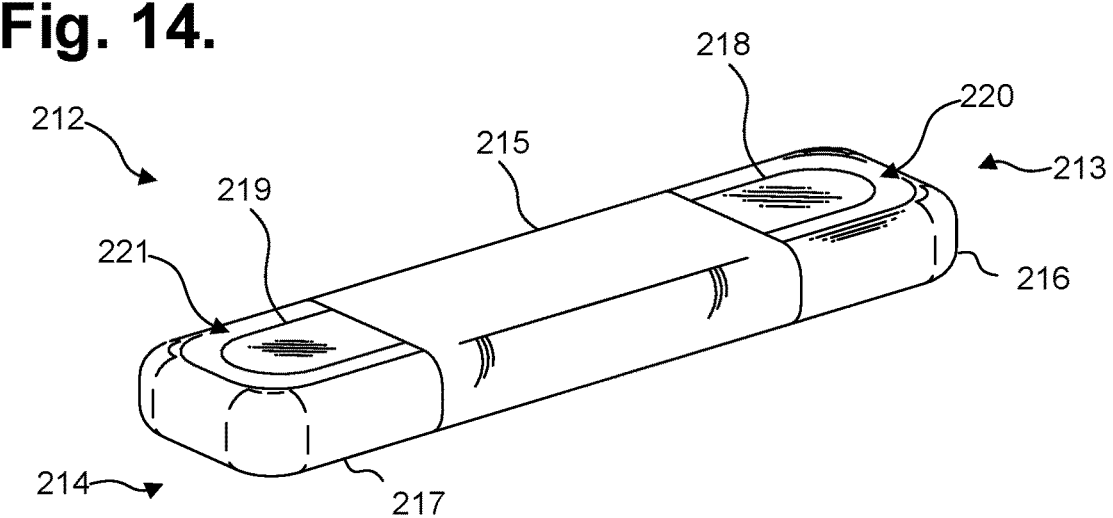
FIG. 14 is a bottom perspective view showing the ICM of FIG. 12 in accordance with a further embodiment.

Despite the challenges faced in capturing low amplitude cardiac action potentials, the ICM 212 is able to operate effectively using only two electrodes that are strategically sized and placed in locations ideally suited to high fidelity P-wave signal acquisition. This approach has been shown to clinically outperform more typical multi-lead monitors because of the improved P-wave clarity, as discussed in W. M. Smith et al., cited supra. FIGS. 13 and 14 are respectively top and bottom perspective views showing the ICM 212 of FIG. 1. Physically, the ICM 212 is constructed with a hermetically sealed implantable housing 215 with at least one ECG electrode forming a superior pole on the proximal end 213 and at least one ECG electrode forming an inferior pole on the distal end 214.

When implanted, the housing 215 is oriented most cephalad. The housing 215 is constructed of titanium, stainless steel or other biocompatible material. The housing 215 contains the sensing, recordation and interfacing circuitry of the ICM 212, plus a long life battery. A wireless antenna is integrated into or within the housing 215 and can be positioned to wrap around the housing's internal periphery or location suited to signal reception. Other wireless antenna placement or integrations are possible.

Physically, the ICM 212 has four ECG electrodes 216, 217, 218, 219. There could also be additional ECG electrodes, as discussed infra. The ECG electrodes include two ventral (or dorsal) ECG electrodes 218, 219 and two wraparound ECG electrodes 216, 217. One ventral ECG electrode 218 is formed on the proximal end 213 and one ventral ECG electrode 219 is formed on the distal end 214. One wraparound ECG electrode 216 is formed circumferentially about the proximal end 213 and one wraparound ECG electrode 217 is formed circumferentially about the distal end 214. Each wraparound ECG electrode 216, 217 is electrically insulated from its respective ventral ECG electrode 218, 219 by a periphery 220, 221.

The four ECG electrodes 216, 217, 218, 219 are programmatically controlled by a microcontroller through onboard firmware programming to enable a physician to choose from several different electrode configurations that vary the electrode surface areas, shapes, and inter-electrode spacing. The sensing circuitry can be programmed, either pre-implant or in situ, to use different combinations of the available ECG electrodes (and thereby changing electrode surface areas, shapes, and inter-electrode spacing), including pairing the two ventral ECG electrodes 216, 217, the two wraparound ECG electrodes 218, 219, or one ventral ECG electrode 216, 217 with one wraparound ECG electrode 218, 219 located on the opposite end of the housing 215. In addition, the periphery 220, 221 can be programmatically controlled to logically combine the wraparound ECG electrode 216, 217 on one end of the ICM 212 with its corresponding ventral ECG electrode 218, 219 to form a single virtual ECG electrode with larger surface area and shape. (Although electronically possible, the two ECG electrodes that are only on one end of the ICM 212, for instance, wraparound ECG electrode 216 and ventral ECG electrode 218, could be paired; however, the minimal inter-electrode spacing would likely yield a signal of poor fidelity in most situations.)

In a further embodiment, the housing 215 and contained circuitry can be provided as a standalone ICM core assembly to which a pair of compatible ECG electrodes can be operatively coupled to form a full implantable ICM device.

Figure 15:
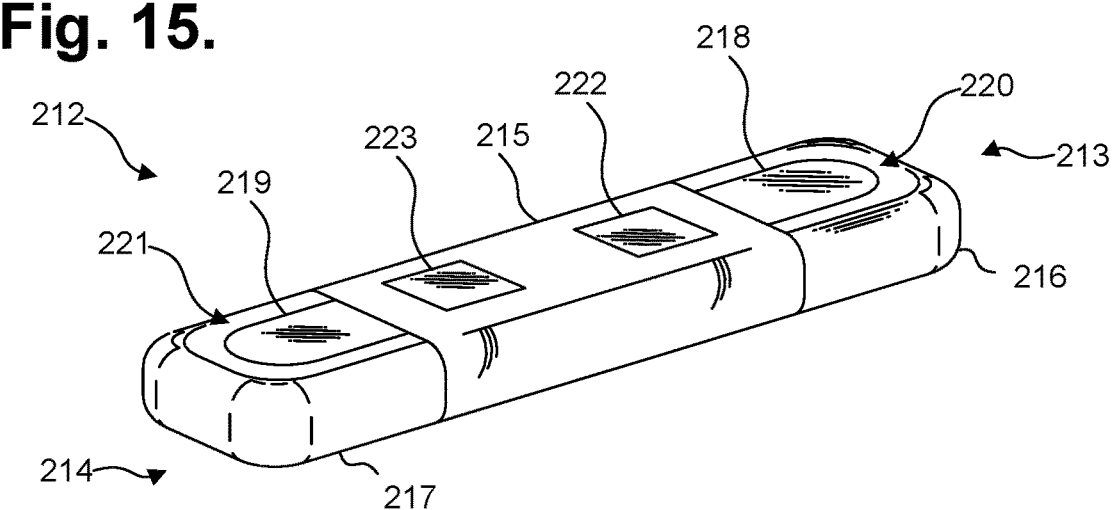
FIGS. 15 and 16 are respectively top and bottom perspective views showing an ICM in accordance with a still further embodiment.

Other ECG electrode configurations are possible. For instance, additional ECG electrodes can be provided to increase the number of possible electrode configurations, all of which are to ensure better P-wave resolution. FIG. 15 is a bottom perspective view showing the ICM 212 of FIG. 12 in accordance with a further embodiment. An additional pair of ventral ECG electrodes 222, 223 are included on the housing's ventral surface. These ventral ECG electrodes 222, 223 are spaced closer together than the ventral ECG electrodes 218, 219 on the ends of the housing 215 and a physician can thus choose to pair the two inner ventral ECG electrodes 222, 223 by themselves to allow for minimal electrode-to-electrode spacing, or with the other ECG electrodes 216, 217, 218, 219 to vary electrode surface areas, shapes, and inter-electrode spacing even further to explore optimal configurations to acquire the P-wave.

Figure 16:
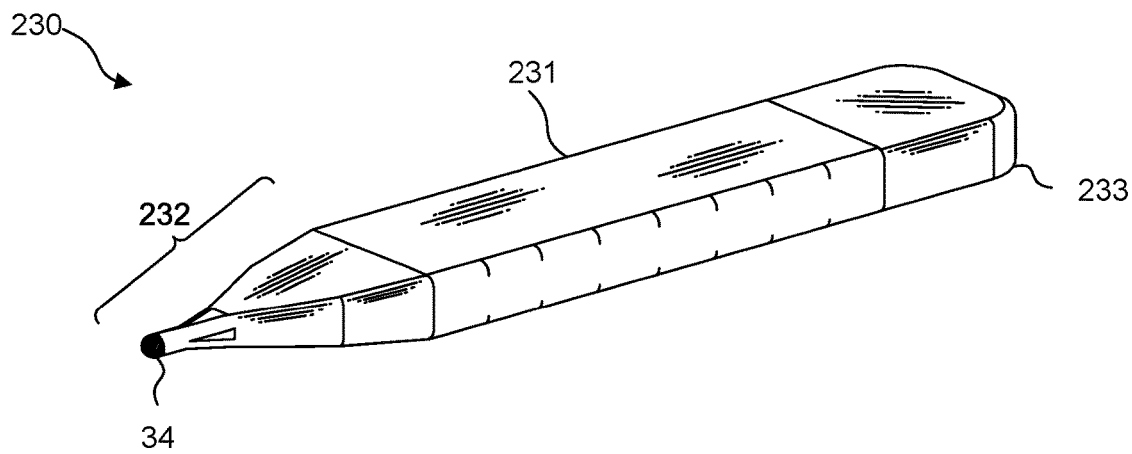
Figure 17:
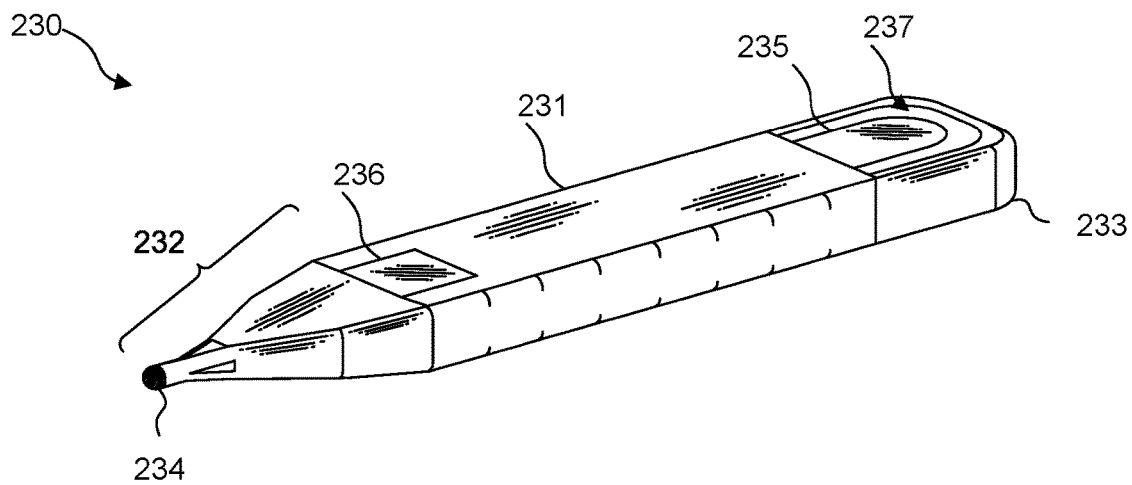
FIG. 17 is a plan view showing further electrode configurations.

Other housing configurations of the ICM are possible. For instance, the housing of the ICM can be structured to enhance long term comfort and fitment, and to accommodate a larger long life battery or more circuitry or features, including physiologic sensors, to provide additional functionality. FIGS. 16 and 17 are respectively top and bottom perspective views showing an ICM 230 in accordance with a still further embodiment. The ICM 230 has a housing 231 with a tapered extension 232 that is terminated on the distal end with an electrode 234. On a proximal end, the housing 231 includes a pair of ECG electrodes electrically insulated by a periphery 237 that include a ventral ECG electrode 233 and a wraparound ECG electrode 234. In addition, a ventral ECG electrode 236 is oriented on the housing's distal end before the tapered extension 232. Still other housing structures and electrode configurations are possible.

In general, the basic electrode layout is sufficient to sense cardiac action potentials in a wide range of patients. Differences in thoracic tissue density and skeletal structure from patient to patient, though, can affect the ability of the sensing electrodes to efficaciously capture action potential signals, yet the degree to which signal acquisition is affected may not be apparent until after an ICM has been implanted and deployed, when the impacts of the patient's physical constitution and his patterns of mobility and physical movement on ICM monitoring can be fully assessed.

Figure 18:
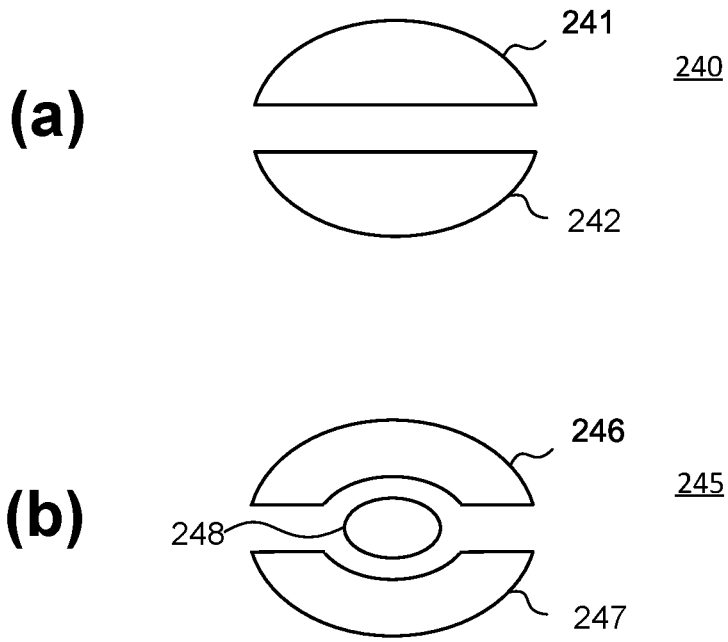
FIG. 18 is a functional block diagram showing the P-wave focused component architecture of the circuitry of the ICM of FIG. 12.

In further embodiments, the electrodes can be configured post-implant to allow the ICM to better adapt to a particular patient's physiology. For instance, electrode configurations having more than two sensing electrodes are possible. FIG. 18 is a plan view showing further electrode configurations. Referring first to FIG. 18(a), a single disc ECG electrode 240 could be bifurcated to form a pair of half-circle ECG electrodes 241, 242 that could be programmatically selected or combined to accommodate a particular patients ECG signal characteristics post-ICM implant. Referring next to FIG. 18(b), a single disc ECG electrode 245 could be divided into three sections, a pair of crescent-shaped ECG electrodes 246, 247 surrounding a central semicircular ECG electrode 248 that could similarly be programmatically selected or combined. Still other ECG electrode configurations are possible.

Figure 19:
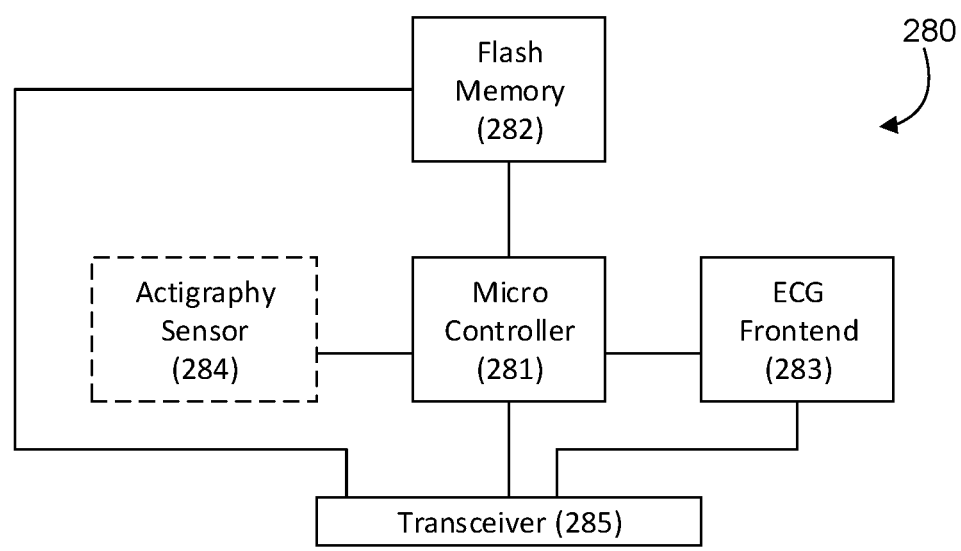
FIG. 19 is a functional block diagram showing a system for wirelessly interfacing with an ICM in accordance with one embodiment.

ECG monitoring and other functions performed by the ICM 212 are provided through a micro controlled architecture. FIG. 19 is a functional block diagram showing the P-wave focused component architecture of the circuitry 280 of the ICM 212 of FIG. 12. The circuitry 280 is powered through the long life battery 21 provided in the housing 215, which can be a direct current battery. Operation of the circuitry 280 of the ICM 212 is managed by a microcontroller 281, such as the EFM32 Tiny Gecko 32-bit microcontroller, manufactured by Silicon Laboratories Inc., Austin, Tex. The microcontroller 281 has flexible energy management modes and includes a direct memory access controller and built-in analog-to-digital and digital-to-analog converters (ADC and DAC, respectively). The microcontroller 281 also includes a program memory unit containing internal flash memory (not shown) that is readable, writeable, and externally programmable.

The microcontroller 281 operates under modular micro program control as specified in firmware stored in the internal flash memory. The microcontroller 281 draws power from the battery provided in the housing 215 and connects to the ECG front end circuit 63. The front end circuit 63 measures raw subcutaneous electrical signals using a driven reference signal that eliminates common mode noise, as further described infra.

The circuitry 280 of the ICM 212 also includes a flash memory 282 external to the microcontroller 281, which the microcontroller 281 uses for continuously storing samples of ECG monitoring signal data and other physiology, such as respiratory rate, blood oxygen saturation level ($SpO_2$), blood pressure, temperature sensor, and physical activity, and device and related information. The flash memory 282 also draws power from the battery provided in the housing 215. Data is stored in a serial flash memory circuit, which supports read, erase and program operations over a communications bus. The flash memory 282 enables the microcontroller 281 to store digitized ECG data. The communications bus further enables the flash memory 282 to be directly accessed wirelessly through a transceiver 285 coupled to an antenna 217 built into (or provided with) the housing 215. The transceiver 285 can be used for wirelessly interfacing over Bluetooth or other types of wireless technologies for exchanging data over a short distance with a paired mobile device, including smartphones and smart watches, that are designed to communicate over a public communications infrastructure, such as a cellular communications network, and, in a further embodiment, other wearable (or implantable) physiology monitors, such as activity trackers worn on the wrist or body. Other types of device pairings are possible, including with a desktop computer or purpose-built bedside monitor. The transceiver 285 can be used to offload stored ECG monitoring data and other physiology data and information and for device firmware reprogramming. In a further embodiment, the flash memory 282 can be accessed through an inductive coupling (not shown).

The microcontroller 281 includes functionality that enables the acquisition of samples of analog ECG signals, which are converted into a digital representation, implementing the method 100 described supra with reference to FIG. 10. In one mode, the microcontroller 281 implements a loop recorder feature that will acquire, sample, digitize, signal process, and store digitized ECG data into available storage locations in the flash memory 282 until all memory storage locations are filled, after which existing stored digitized ECG data will either be overwritten through a sliding window protocol, albeit at the cost of potentially losing the stored data that was overwritten, if not previously downloaded, or transmitted wirelessly to an external receiver to unburden the flash memory. In another mode, the stored digitized ECG data can be maintained permanently until downloaded or erased to restore memory capacity. Data download or erasure can also occur before all storage locations are filled, which would free up memory space sooner, albeit at the cost of possibly interrupting monitoring while downloading or erasure is performed. Still other modes of data storage and capacity recovery are possible.

The circuitry 280 of the ICM 212 can include functionality to programmatically select pairings of sensing electrodes when the ICM 212 is furnished with three or more electrodes. In a further embodiment, multiple sensing electrodes could be provided on the ICM 212 to provide a physician the option of fine-tuning the sensing dipole (or tripole or multipole) in situ by parking active electrodes and designating any remaining electrodes inert. The pairing selection can be made remotely through an inductive coupling or by the transceiver 285 via, for instance, a paired mobile device, as further described infra. Thus, the sensing electrode configuration, including number of electrodes, electrode-to-electrode spacing, and electrode size, shape, surface area, and placement, can be modified at any time during the implantation of the ICM 212.

In a further embodiment, the circuitry 280 of the ICM 212 can include an actigraphy sensor 284 implemented as a 3-axis accelerometer. The accelerometer may be configured to generate interrupt signals to the microcontroller 281 by independent initial wake up and free fall events, as well as by device position. In addition, the actigraphy provided by the accelerometer can be used during post-monitoring analysis to correct the orientation of the ICM 212 if, for instance, the ICM 212 has been inadvertently implanted upside down, that is, with the ICM's housing oriented caudally, as well as for other event occurrence analyses.

In a still further embodiment, the circuitry 280 of the ICM 212 can include one or more physiology sensors. For instance, a physiology sensor can be provided as part of the circuitry 280 of the ICM 212, or can be provided on the electrode assembly 214 with communication with the microcontroller 281 provided through a circuit trace. The physiology sensor can include an $SpO_2$ sensor, blood pressure sensor, temperature sensor, respiratory rate sensor, glucose sensor, airflow sensor, volumetric pressure sensing, or other types of sensor or telemetric input sources.

In a yet further embodiment, firmware with programming instructions, including machine learning and other forms of artificial intelligence-originated instructions, can be downloaded into the microcontroller's internal flash memory. The firmware can include heuristics to signal patient and physician with alerts over health conditions or arrhythmias of selected medical concern, such as where a heart pattern particular to the patient is identified and the ICM 212 is thereby reprogrammed to watch for a reoccurrence of that pattern, after which an alert will be generated and sent to the physician (or other caregiver) through the transceiver 285 via, for instance, a paired mobile device. Similarly, the firmware can include heuristics that can be downloaded to the ICM 212 to actively identify or narrow down a pattern (or even the underlying cause) of sporadic cardiac conditions, for instance, atrial tachycardia (AT), atrial fibrillation (AF), atrial flutter (AFL), AV node reciprocating tachycardia, ventricular tachycardia (VT), sinus bradycardia, asystole, complete heart block, and other cardiac arrhythmias, again, after which an alert will be generated and sent to the physician (or other caregiver) through the transceiver 285. For instance, an alert that includes a compressed ECG digitized sample can also be wirelessly transmitted by the ICM 212 upon the triggering of a preset condition, such as an abnormally low heart rate in excess of 170 beats per minute (bpm), an abnormally low heart rate falling below 30 bpm, or AF detected by onboard analysis of RR interval variability by the microcontroller 281. Finally, a similar methodology of creating firmware programming tailored to the monitoring and medical diagnostic needs of a specific patient (or patient group or general population) can be used for other conditions or symptoms, such as syncope, palpitations, dizziness and giddiness, unspecified convulsions, abnormal ECG, transient cerebral ischemic attacks and related syndromes, cerebral infarction, occlusion and stenosis of pre-cerebral and cerebral arteries not resulting in cerebral infarction personal history of transient ischemic attack, and cerebral infarction without residual deficits, to trigger an alert and involve the physician or initiate automated analysis and follow up back at the patient's clinic. Finally, in a still further embodiment, the circuitry 280 of the ICM 212 can accommodate patient-interfaceable components, including an external tactile feedback device (not shown) that wirelessly interfaces to the ICM 212 through the transceiver 285. A patient 210 can press the external tactile feedback device to mark events, such as a syncope episode, or to perform other functions. The circuitry 280 can also accommodate triggering an external buzzer 67, such as a speaker, magnetic resonator or piezoelectric buzzer, implemented as part of the external tactile feedback device or as a separate wirelessly-interfaceable component. The buzzer 67 can be used by the microcontroller 281 to indirectly output feedback to a patient 210, such as a low battery or other error condition or warning. Still other components, provided as either part of the circuitry 280 of the ICM 212 or as external wirelessly-interfaceable devices, are possible.

The ECG front end circuit 283 of the ICM 12 measures raw subcutaneous electrical signals using a driven reference signal, such as described in U.S. Pat. Nos. 9,700,227, 9,717,433, and 9,615,763, cited supra. The driven reference signal effectively reduces common mode noise, power supply noise and system noise, which is critical to preserving the characteristics of low amplitude cardiac action potentials, especially the P wave signals originating from the atria.

The ECG front end circuit 283 is organized into a passive input filter stage, a unity gain voltage follower stage, a passive high pass filtering stage, a voltage amplification and active filtering stage, and an anti-aliasing passive filter stage, plus a reference generator. The passive input filter stage passively shifts the frequency response poles downward to counter the high electrode impedance from the patient on the signal lead and reference lead, which reduces high frequency noise. The unity gain voltage follower stage allows the circuit to accommodate a very high input impedance, so as not to disrupt the subcutaneous potentials or the filtering effect of the previous stage. The passive high pass filtering stage includes a high pass filter that removes baseline wander and any offset generated from the previous stage. As necessary, the voltage amplification and active filtering stage amplifies or de-amplifies (or allows to pass-through) the voltage of the input signal, while applying a low pass filter. The anti-aliasing passive filter stage provides an anti-aliasing low pass filter. The reference generator drives a driven reference signal containing power supply noise and system noise to the reference lead and is connected directly to the patient, thereby avoiding the thermal noise of the protection resistor that is included as part of the protection circuit.

Figure 20:
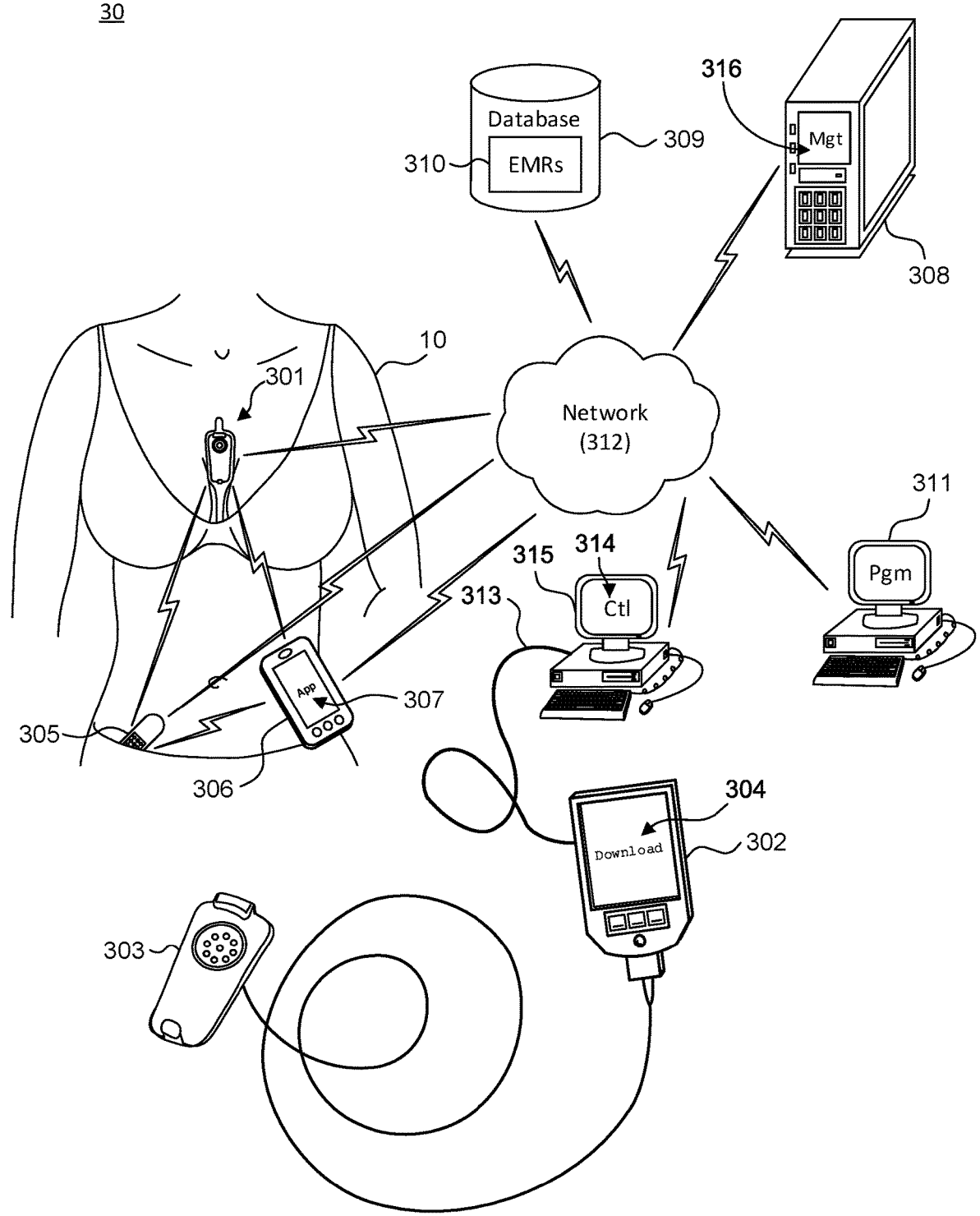
FIG. 20 is a functional block diagram showing a system 300 for obtaining ECG data from a cardiac monitor, in accordance with one embodiment.

Once collected, the ECG data is offloaded from the cardiac monitor to a database, computer, or mobile device via a wired or wireless connection. The ECG data can be stored or collected in real time, and can be transferred through a physical connection, a short-range wireless connection, or a network-based connection. FIG. 20 is a functional block diagram showing a system 300 for obtaining ECG data from a cardiac monitor, in accordance with one embodiment. The cardiac monitor 301 can be dermally positioned on a patient or can be implanted for monitoring ECG data, which can be offloaded for storage and further processing.

Physical Download Station

In one embodiment, when dermally positioned, the cardiac monitor 301 can be connected to a download station 302, which could be a programmer or other device that permits the retrieval of stored ECG monitoring data, execution of diagnostics on or programming of the monitor 301, or performance of other functions, via a receptacle 303. In turn, the download station 125 executes a communications or offload program 304 ("Offload") or similar program that interacts with the cardiac monitor 301 via the physical interface to retrieve the stored ECG monitoring data. The download station 302 could be a server, personal computer, tablet or handheld computer, smart mobile device, or purpose-built programmer designed specific to the task of interfacing with a monitor recorder 14. Still other forms of download stations 302 are possible. Generally, the download station is located in a physician's office, in which the patient must be present. Alternatively, the patient can send in the dermal device for offloading the ECG data. Whether the patient is located in the office or sends in the device, real-time ECG data cannot be accessed since the cardiac monitor is removed from the patient.

Upon retrieving stored ECG monitoring data from the cardiac monitor 301, middleware first operates on the retrieved data to adjust the ECG capture quality, as necessary, and to convert the retrieved data into a format suitable for use by third party post-monitoring analysis software. The formatted data can then be retrieved from the download station 302 over a hard link 313 using a control program 314 ("Ctl") or analogous application executing on a personal computer 315 or other connectable computing device, via a communications link (not shown), whether wired or wireless, or by physical transfer of storage media (not shown). The personal computer 315 or other connectable device may also execute middleware that converts ECG data and other information into a format suitable for use by a third-party post-monitoring analysis program. In a further embodiment, the download station 302 is able to directly interface with other devices over a computer communications network 312, which could be some combination of a local area network and a wide area network, including the Internet, over a wired or wireless connection.

A client-server model could be used to employ a server 308 to remotely interface with the download station 302 over the network 312 and retrieve the formatted data or other information. The server 308 executes a patient management program 316 ("Mgt") or similar application that stores the retrieved formatted data and other information in a secure database 309 cataloged in that patient's EMRs 310. The patient management program 316, or other trusted application, also maintains and safeguards the secure database 309 to limit access to patient EMRs 310 to only authorized parties for appropriate medical or other uses, such as mandated by state or federal law, such as under the Health Insurance Portability and Accountability Act (HIPAA) or per the European Union's Data Protection Directive.

Short-Range Wireless Connection

In a further embodiment, the cardiac monitor 301, whether dermally positioned or implanted, can interoperate wirelessly with other wearable physiology and activity sensors 305 and with wearable or mobile communications devices 306. Further, the cardiac monitor can function as a physiological monitor to measure not only ECG data, but other types of physiological measures, such as oxygen levels and blood glucose levels. Other types of physiological monitors and measures are possible. Wearable physiology and activity sensors 305 encompass a wide range of wirelessly interconnectable devices that measure or monitor data physical to the patient's body, such as heart rate, temperature, blood pressure, and so forth; physical states, such as movement, sleep, footsteps, and the like; and performance, including calories burned or estimated blood glucose level. These devices originate both within the medical community to sense and record traditional medical physiology that could be useful to a physician in arriving at a patient diagnosis or clinical trajectory, as well as from outside the medical community, from, for instance, sports or lifestyle product companies who seek to educate and assist individuals with self-quantifying interests.

Each of the wearable physiology and activity sensors and the wearable or mobile communications devices can communicate via a short-range wireless connection, such as Bluetooth, with the cardiac monitor. However, due to the short-range connection, the patient must be proximate to the sensors and the communications devices.

The wearable physiology and activity sensor 305 and the wearable or mobile communications devices 306 could also serve as a conduit for providing the data collected by the wearable physiology and activity sensor 305 to a server 308. The server 308 could then merge the collected data into the wearer's electronic medical records, EMRs, 310 in the secure database 309, if appropriate (and permissible), or the server 308 could perform an analysis of the collected data, perhaps based by comparison to a population of like wearers of the wearable physiology and activity sensor 305. Further, the ECG data can be provided to a remotely located physician or other medical professional for review. However, even though the ECG data may be transferred in real time from the cardiac monitor to the wearable physiology and activity sensor 305 or the wearable or mobile communications devices 306 via Bluetooth, the ECG data is delayed to the remote physician due to the authentication required when the data is transferred over the network to the server.

Alternatively, the wearable physiology and activity sensors 305 are capable of wireless interfacing with wearable or mobile communications devices 306, particularly smart mobile devices, including so-called "smart phones," to download monitoring data either in real-time or in batches. The wearable or mobile communications device 306 executes an application ("App") 307 that can retrieve the data collected by the wearable physiology and activity sensor 305 and evaluate the data to generate information of interest to the wearer, such as an estimation of the effectiveness of the wearer's exercise efforts. Still other wearable or mobile communications device 306 functions on the collected data are possible.

In a further embodiment, a wireless data transfer device can be placed over the patient's chest at a location of the cardiac monitor 301 and the ECG data can be transferred to a computer or mobile device via the wireless data transfer device. In one embodiment, such transfer of data can occur via Bluetooth since the patient must be located in the physician's office or medical facility. The ECG data can subsequently be transferred from the data transfer device to a server via a network. As described above, transfer of the ECG data over the network to a web server is delayed due to the authentication process.

Network-Based Communication

In addition, the cardiac monitor 301 could wirelessly interface directly with the server 308, personal computer 311, or other computing device connectable over the network 312, when the cardiac monitor 301 is appropriately equipped for interfacing with such devices. However, a delay of the data is created and a remote medical professional is unable to access the ECG data in real time. Specifically, in internet-based connections, such as between the puck or cardiac monitor to the web server, the transfer of ECG data is too slow to provide real-time or near real-time streaming of the data to a remote viewer, such as a medical professional. Generally, for real-time or near real-time viewing of ECG data a one second delay or shorter is required. When the ECG data is first transferred to a web server via a network, a secure connection must be established, such as via the TLS Handshake Protocol that is responsible for authenticating new secure sessions and resuming previous secure sessions. Although secure, such connection requires time to establish, which delays the ECG data being accessed and provided to the physician or medical professional.

Figure 21:
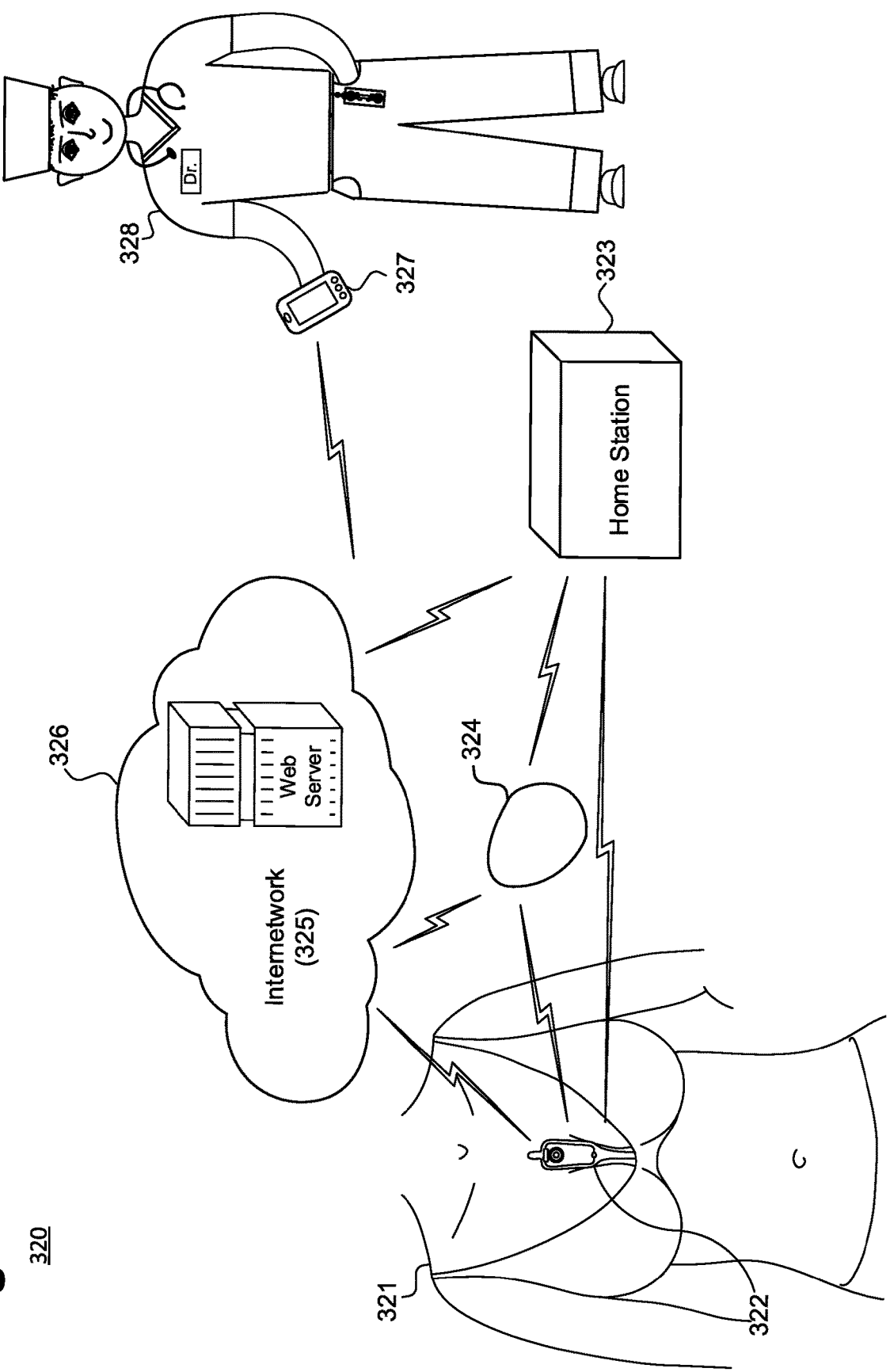
FIG. 21 is a functional block diagram showing a system 320 for real-time remote streaming of ECG data, in accordance with one embodiment.

To reduce the amount of time establishing a connection for the transfer of ECG data, a continuous data connection can be established. FIG. 21 is a functional block diagram showing a system 320 for real-time remote streaming of ECG data, in accordance with one embodiment. A cardiac monitor 322 is dermally positioned or implanted in a patient 321 to capture cardiac action potentials sensed by ECG sensing electrodes which are output as ECG signals. The cardiac monitor 322 can include, at a minimum, a pair of electrodes, a battery, processor, front end, memory, and a wireless transceiver. In one embodiment, the wireless transceiver can include a Near-field communication (NFC) chip that controls the exchange of data between the cardiac monitor 322 and external devices at a short-range, though other communication protocols can also be used by the transceiver at a short range. The presence of NFC or other communication protocols allows the wireless transceiver to implement a cryptographic security protocol with an external device, protecting data being exchanged.

In one embodiment, the ECG data can be offloaded directly from the cardiac monitor 322 via a wireless connection, over an internetwork 325, such as the Internet, to a server 326 in the cloud. Specifically, the ECG data is first encrypted by the cardiac monitor, such as via the NFC chip, and a continuous connection is established with the cloud server 326. The cloud server 326 then transfers the ECG data in real time to a physician or other medical professional 328 via a computing device, such as a computer, tablet, or cellular phone 327.

In a further embodiment, a data transfer device, such as a puck 324, can be used to obtain data from the cardiac monitor 322. The puck 324 can be shaped as a circle, oval, or computer mouse, and can be pressed against (or held close to) the patient's chest in the parasternal region over the cardiac monitor 322 to access ECG data and provide charging to the cardiac monitor 322. Other shapes of the puck 324 are possible. At a minimum, the puck should include a housing, processor, battery, memory, and a wireless transceiver or NFC chip. The puck 324 can access the ECG data from the cardiac monitor 322 via the wireless transceiver or an NFC chip. If the ECG data is not already encrypted, the puck 324 can encrypt the ECG data. Once obtained, the puck 324 can transmit the encrypted ECG data to the cloud server 326 or to a home station 323.

Specifically, the puck 324 can include a data download module (not shown), which uses an internal wireless transceiver to wirelessly download data collected by the cardiac monitor 322 by interfacing with the wireless transceiver cardiac monitor. The downloading of the ECG data can happen simultaneously to charging of the cardiac monitor by the puck, as described below. The downloaded physiological data can in turn be wirelessly forwarded to a home station or the cloud server.

The home station 323 can be located at the patient's home, such as near the patient's bed, and can include a housing, processor, inductive battery charger, control circuit, memory, and wireless transceiver or NFC chip. The home station 323 can be used to communicate data to and from the cardiac monitor 322, program the cardiac monitor, and charge the puck 324. The data can include ECG data, as well as other types of physiological data, obtained by the cardiac monitor, such as respirator rate, blood glucose levels, and oxygen levels, and can be collected at least once a day or over longer periods of time. In a further embodiment, the cardiac monitor 322 can communicate the ECG data and physiological data directly to the home station 323, without the use of the puck 324.

Cardiac or other types of physiological monitors, whether dermally placed on a patient or implanted, are not usually responsible for creating or initiating a secure communication channel, but can do so by including a cryptographic key or a series of cryptographic keys in the cardiac monitor. The cryptographic key would allow communication to be encrypted and to only be decrypted by an authorized receiver such as a cloud server. All the data, including ECG and other physiological data, transferred between the cardiac monitor and cloud server would be encrypted with the encryption based on the keys stored in the server and device, even if the data first goes through a gateway, the gateway would be unable to decrypt the data. The cardiac and physiological monitors can be positioned dermally on a patient or implanted, such as those devices described in detail in U.S. Provisional Patent Application No. 62/874,086, filed Jul. 15, 2019; U.S. Provisional Patent Application No. 62/873,740, filed Jul. 12, 2019; and U.S. Provisional Patent Application No. 62/962,773, filed Jan. 17, 2020, the disclosures of which are incorporated by reference and cover a configurable hardware platform for health and medical monitoring of physiology that is housed within a hermetically sealed implantable medical device (IMD). In one embodiment, the IMD is equipped with one or more physiological sensors that non-exhaustively include ECG, temperature, oxygen saturation, respiration, and blood glucose. Physically, the IMD has a generally tubular shape that includes a central tubular body with rounded semi spherical ends. When configured to measure electrocardiographic signals, the central tubular body and one of the semi spherical ends function as electrode dipoles. That semi spherical end is electrically conductive yet electrically insulated from the central tubular body. As well, the outside surface of the central tubular body is partially electrically insulated, generally on the surface closest to the electrically conductive semi spherical end to form a non-electrically conductive inversion with only the outside surface distal to that semi spherical end being exposed. When placed within the central tubular body, a foldable printed circuit board (PCB) forms three aspects that respectively define a coil for capture of magnetic fields used in energy transfer, an additional high frequency antenna for radio frequency (RF) data exchange, and a central folded flex circuit containing a microcontroller and device circuitry. A power source that includes a rechargeable battery is also placed within the IMD to one end of the folded PCB and in electrical contact through a protection circuit with the electrically conductive semi spherical end, thereby serving as an electrical feedthrough to the PCB. Another implementation may use the charging antenna as an insulator and to route the electrical signals from the spherical conductive end. The battery may be recharged using a non-contact method, such as inductive charging, resonant charging, energy harvesting, thermal gradient charging, ultrasonic charging, RF-based charging or charging by ambient or driven motion. Different types of recharging processes can be used as described in U.S. Pat. No. 11,116,451, issued Sep. 14, 2021, the disclosure of which is incorporated by reference.

The encrypted ECG data received on the home station 323, from the puck or the cardiac monitor, can be delivered via WiFi or a cellular connection to the cloud server 326 and subsequently, to the physician 328 via a computer, tablet, or cellular phone 327, without compromising data security due to the encryption of the data. The home station 323 maintains a continuous or intermittent connection with the cloud server 326, which does not require authentication of the home station every time, including startup and a handshake protocol, which reduces an amount of time for a remote user, such as the physician, to receive the ECG data. Further, the home station 323 may include an inductive charger to charge the puck when not in use.

When applied to a patient, the energized puck 324 can charge the cardiac monitor 322. For instance, the puck can include an energy transmission module (not shown) to provide input, such as magnetic or radio waves, that provides electrical energy to the cardiac monitor 322 during charging. For example, the energy transmission module can include a radio transmitter that radiates radio waves that can be captured by the cardiac monitor 322, such as via an antenna. Alternatively, the ECG data can be transmitted via an inductive coil (not shown) included in the puck to generate a magnetic field that energizes an inductive coil within the cardiac monitor 322. Charging of the cardiac monitor during data transfer is useful to prevent draining the battery during the transfer and to further power the battery for later use.

ECG streaming is useful for adjusting beat detection and noise detection parameters of the cardiac monitor to ensure that the ECG reports are accurate. Currently, beat detection and noise detection adjustments are made while the patient is present at the physician's office since the adjustments are generally based on real time ECG views. Other parameters, such as arrhythmia detection, can also occur. However, such parameters can be adjusted remotely using the remote real-time ECG streaming. In one example, beat detection can use the amplitude and change in volts per second to identify heart beats of the patient. Certain patterns can fool a beat detector and change the points in an R-R plot. Accordingly, accurately identifying beats is important.

In one embodiment, beat detection can occur on the cardiac monitor. Alternatively or in addition to the monitor, beat detection can occur on a server. The beat detection algorithm for the patient can be improved by comparing the beat detection results from the monitor with the beat detection results from the server. For example, the comparison can occur on the server, which can also do the tuning of the beat detection of the cardiac monitor. The updated beat parameters are then sent to the cardiac monitor. Such comparison can occur daily, such as part of a daily interrogation of data from the cardiac monitor.

In one example, beat detection may need to be adjusted for a patient. For instance, when a patient first receives an ICM, a fibrous capsule has not yet formed and the tissue is bleeding and swollen. As the patient recovers, the patient's cardiac signals usually grow and the beat detection algorithm should be adjusted.

In a further embodiment, direct transfer of ECG data from the cardiac monitor to the home station can also be useful in doctors' offices. For example, patients with cardiac devices are sitting in a waiting room at the physician's office. While waiting, the cardiac devices can encrypt the ECG or other physiological data, and send the encrypted data to a home station located at the physician's office so that the data is readily available when the patient is called to see the doctor. Since the data is encrypted by the cardiac monitor, the data is secure despite the multiple monitors that are offloading data simultaneously. Further, the encrypted data can only be unencrypted in the cloud server.

Although the above has discussed real-time streaming of cardiac data, other types of physiological data can be streamed, oxygen rate, temperature, respiratory rate, blood glucose levels, and more. The monitors for the physiological data can be included on the cardiac monitor or can be separate from the cardiac monitor.

Figure 22:
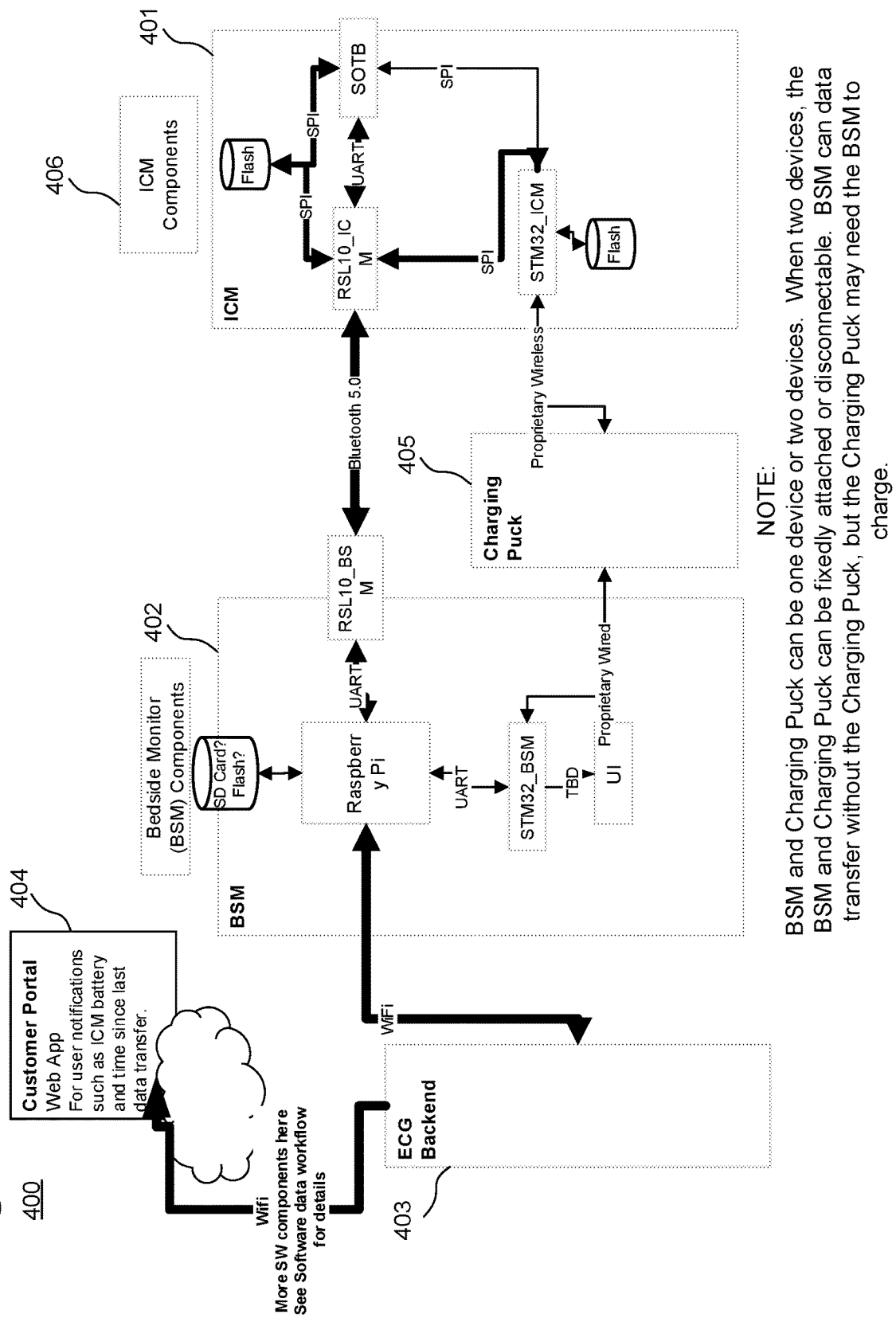
FIG. 22 is a block diagram showing, by way of example, ICM initiated data flow paths.

Data can be communicated between an implantable medical device (IMD), bedside monitor, and ECG backend or directly between an IMD and an ECG backend. The IMD can include a cardiac or physiology monitor, which is dermal or implanted. The terms IMD and ICM are used interchangeably within this application. The ECG backend can be a server that the bedside monitor communications with via WiFi, for example, on a hardware platform such as Raspberry Pi. However, other types of communication and communication devices are possible. The data exchange can be initiated by the IMD or the bedside monitor. FIG. 22 is a block diagram showing, by way of example, ICM initiated data flow paths 400. An ICM 401 can provide ECG data recorded by the ICM device, logs from components 406 of the ICM, and a status of the ICM components 406 to an ECG backend 403 via a bedside monitor 402. The bedside monitor 402 can include a charging puck 405 or the charging puck 405 can be a device separate from the bedside monitor 402. When separate, the bedside monitor 402 and charging puck 405 can be fixedly attached together or disconnectable. The bedside monitor 402 can transfer data without the charging puck 405; however, the charging puck 405 may need the bedside monitor 402 to charge.

In turn, the backend 403 can provide ICM components, firmware updates, and initial charge parameter of the ICM to the ICM 401 via the bedside monitor 402. The backend server 403 can communicate with a customer portal 404, such as a web application, to provide patient notifications, such as amount of ICM battery charge and date or time of last data transfer. The communication between the ECG backend 403 and customer portal 404 can occur via WiFi or other communication means. In one example, the data exchange can occur daily, multiple times a day, or after more than one day.

Figure 23:
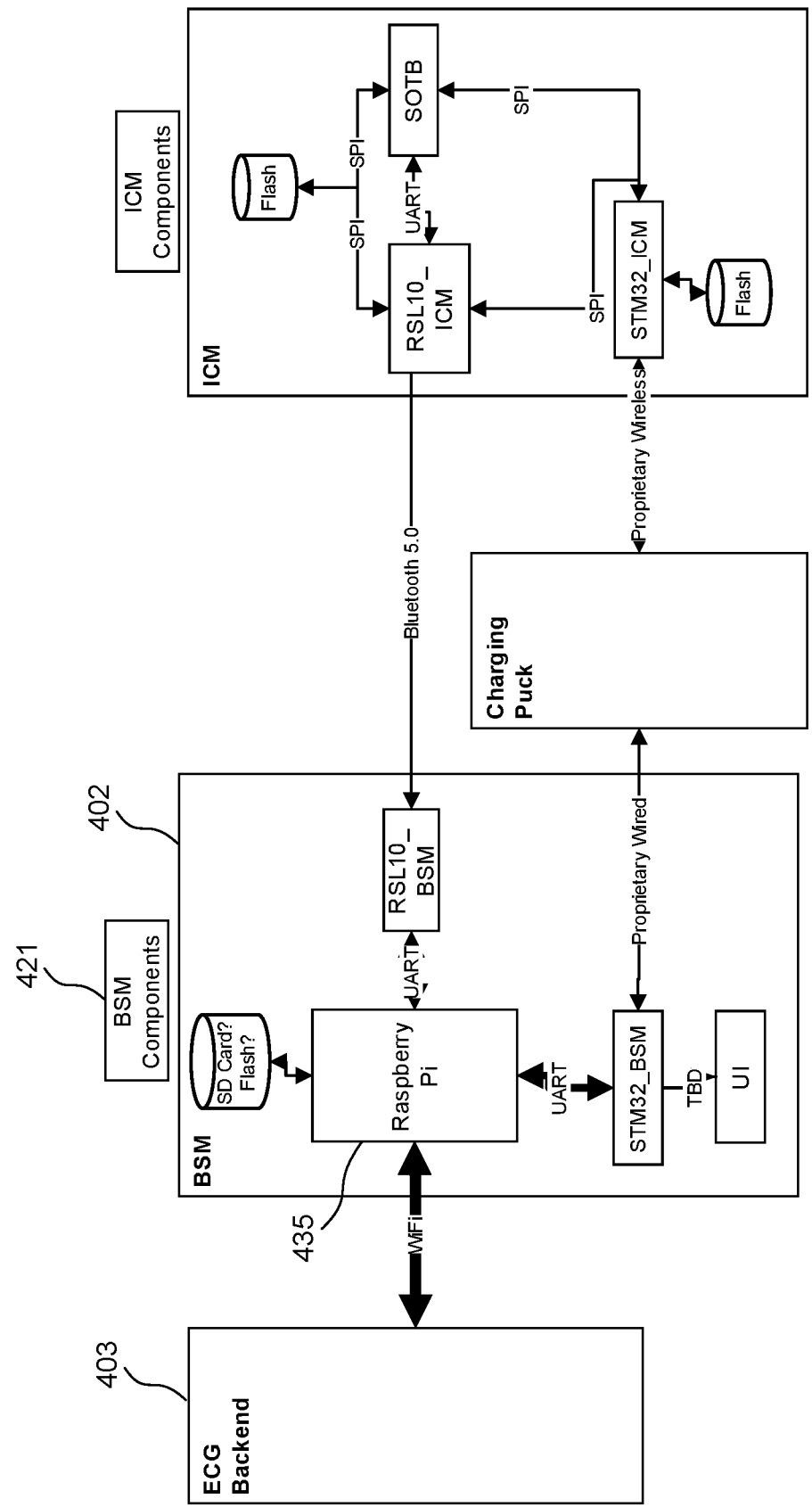
FIG. 23 is a block diagram showing, by way of example, a bedside monitor-initiated data flow.

The bedside monitor can also initiate communication, rather than merely passing data between the ICM and ECG backend. FIG. 23 is a block diagram showing, by way of example, a bedside monitor-initiated data flow 420. The bedside monitor 402 can provide logs from bedside monitor components 421 and a status of the bedside monitor components 421 to the backend server 403, while the backend server 403 can provide the bedside monitor 402 with bedside monitor components and firmware updates. The transfer of data can occur multiple times a day, once a day, or after more than one day.

Figure 24:
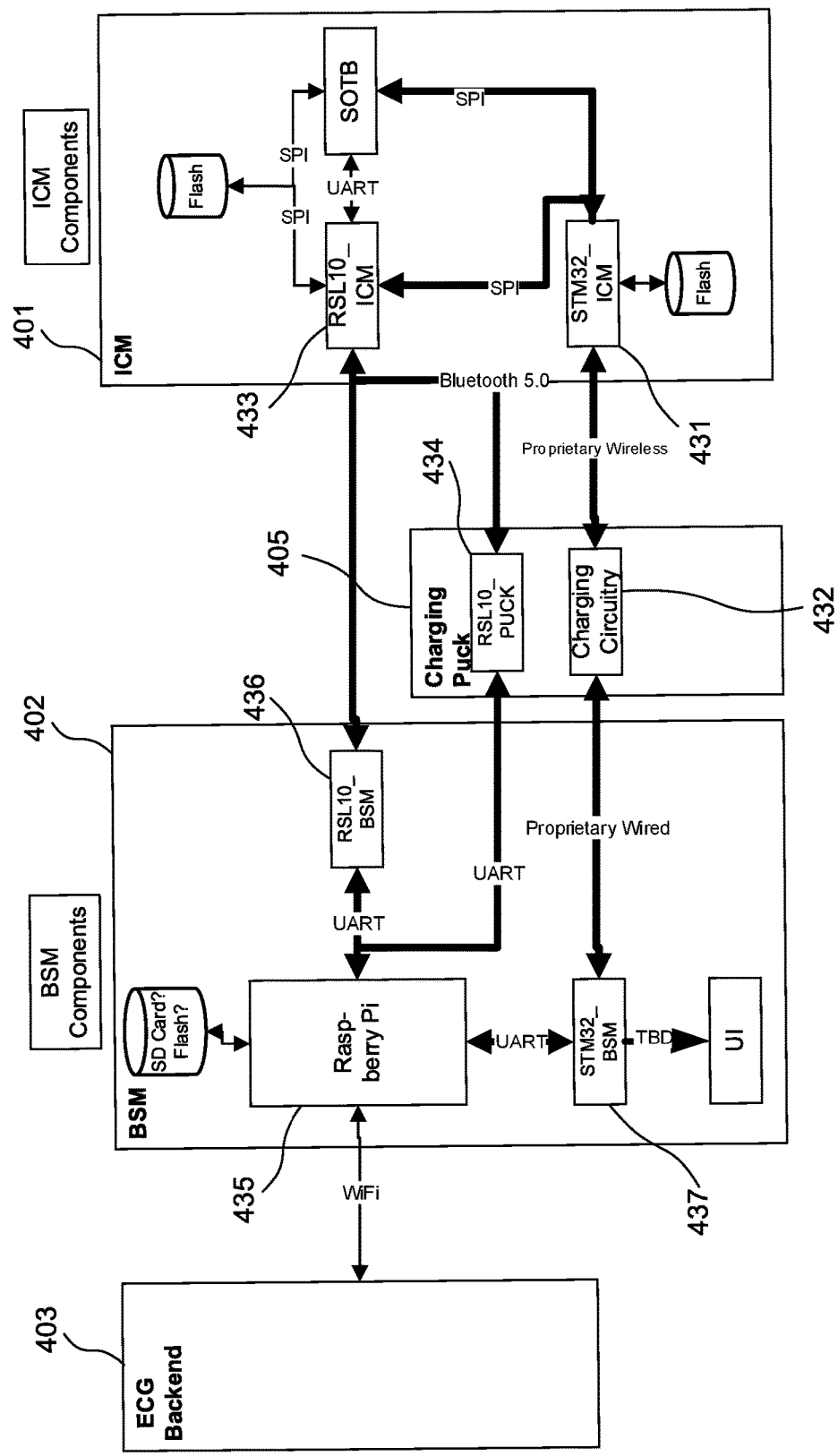
FIG. 24 is a block diagram showing, by way of example, an ICM initiated charging data flow.

The ICM can initiate charging upon identifying a status of low battery, such as communication from the ECG backend, in one embodiment. FIG. 24 is a block diagram showing, by way of example, an ICM initiated charging data flow 430. Charging of the ICM 401 can occur along different paths. For example, a first charging path can include a supervisor chip (STM 32) 431 on the IMD 401, which communicates with charging circuitry 432 on a puck 405 that can be attached to or separate from the bedside monitor 402. In turn, the puck 405 communicates with the bedside monitor 402 via STM 32 437 to control the puck 405 and an amount of charge by generating a wave form via a communication bus (UART), which can be SPI. The charging can be initialized by the IMD 401 by providing charge parameters and updates to the charge parameters. During charging, data can also be communicated between the IM 401 and the bedside monitor 402 via the charge waveforms or by using Bluetooth.

A second charging path can include a Bluetooth module 433, such as the RSL10 SoC manufactured by On Semiconductor, on the IMD 401, which communicates with a Bluetooth module 434 in the puck 405, which then communicates with the bedside monitor 402, such as via a Raspberry Pi hardware platform 435. In a further example, the IMD 401 can be charged directly via the bedside monitor 402 without the puck 405. For instance, the Bluetooth module 433 of the IMD 401 communicates with a Bluetooth module (RSL 10) 436 of the bedside monitor 402.

During charging, data can be transferred from the ICM 401 to the backend server 403 via the bedside monitor 402 or from the backend server 403 to the ICM 401 via the bedside monitor 402. For example, the data can be offloaded from the ICM 401 via Bluetooth during charging based on one or more of the charging paths described above. Alternatively, the data can be transferred via data blanking during which charging can be automatically stopped once a certain amount of charge is reached while the data is transferred and once a predetermined amount of data has been transferred, charging can begin again. The data transfer can occur over multiple cycles of charging, data transfer, charging, data transfer, such as depending on an amount of data to be transferred and a speed of the data transfer.

Figure 25:
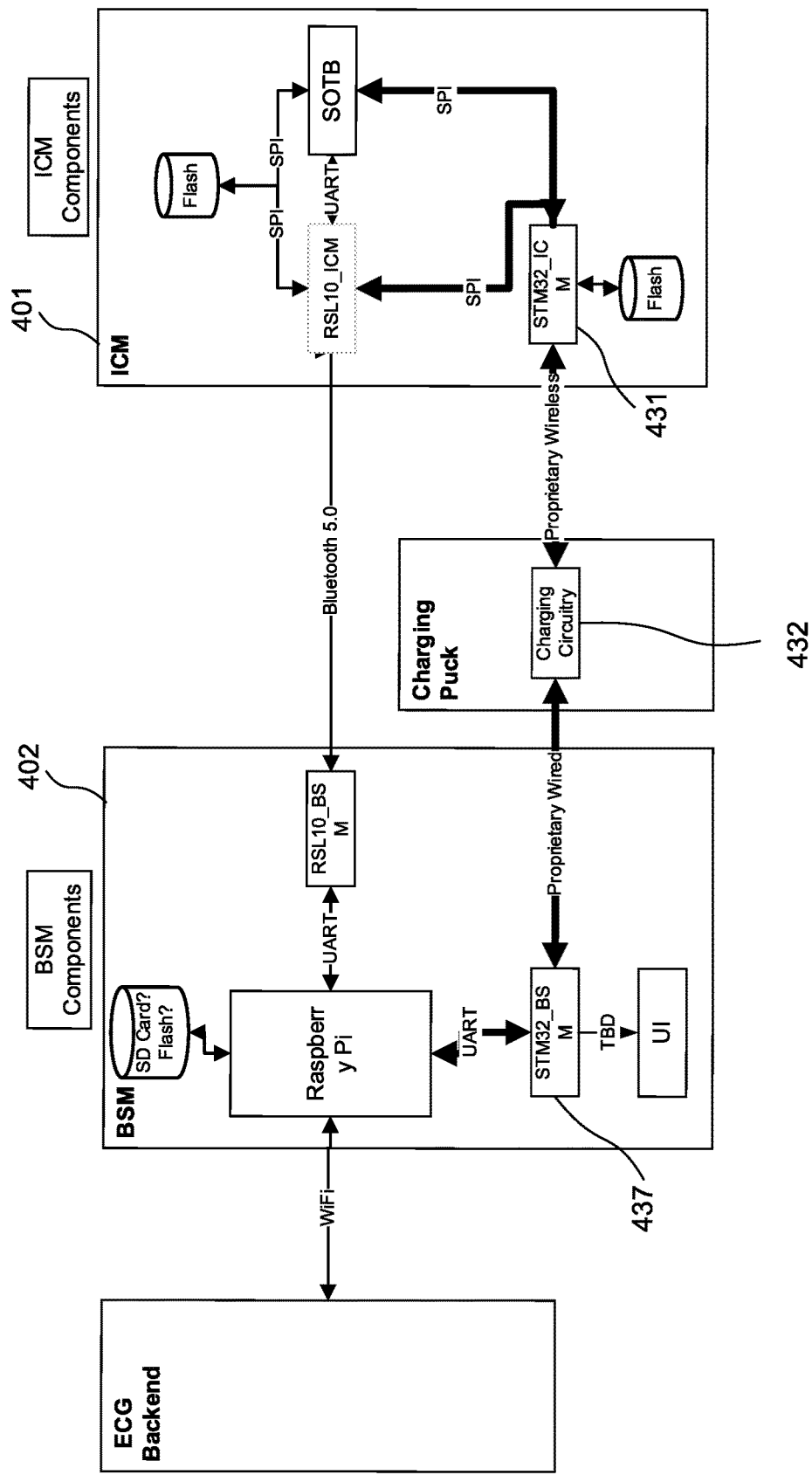
FIG. 25 is a block diagram showing, by way of example, a recovery mode data flow.

When the ICM is not properly functioning, the ICM can contact the bedside monitor for assistance. FIG. 25 is a block diagram showing, by way of example, a recovery mode data flow 440. In recovery mode, the bedside monitor 402 can provide the IMD 401 with debug commands, while the IMD 401 provides error logs and bug reports to the bedside monitor 402. Communication can occur via a path, which includes a supervisor chip (STM 32) 431 on the IMD 401, which communicates with charging circuitry 432 on a puck 405 that communicates with the bedside monitor 402 via STM 32 437.

Figure 26:
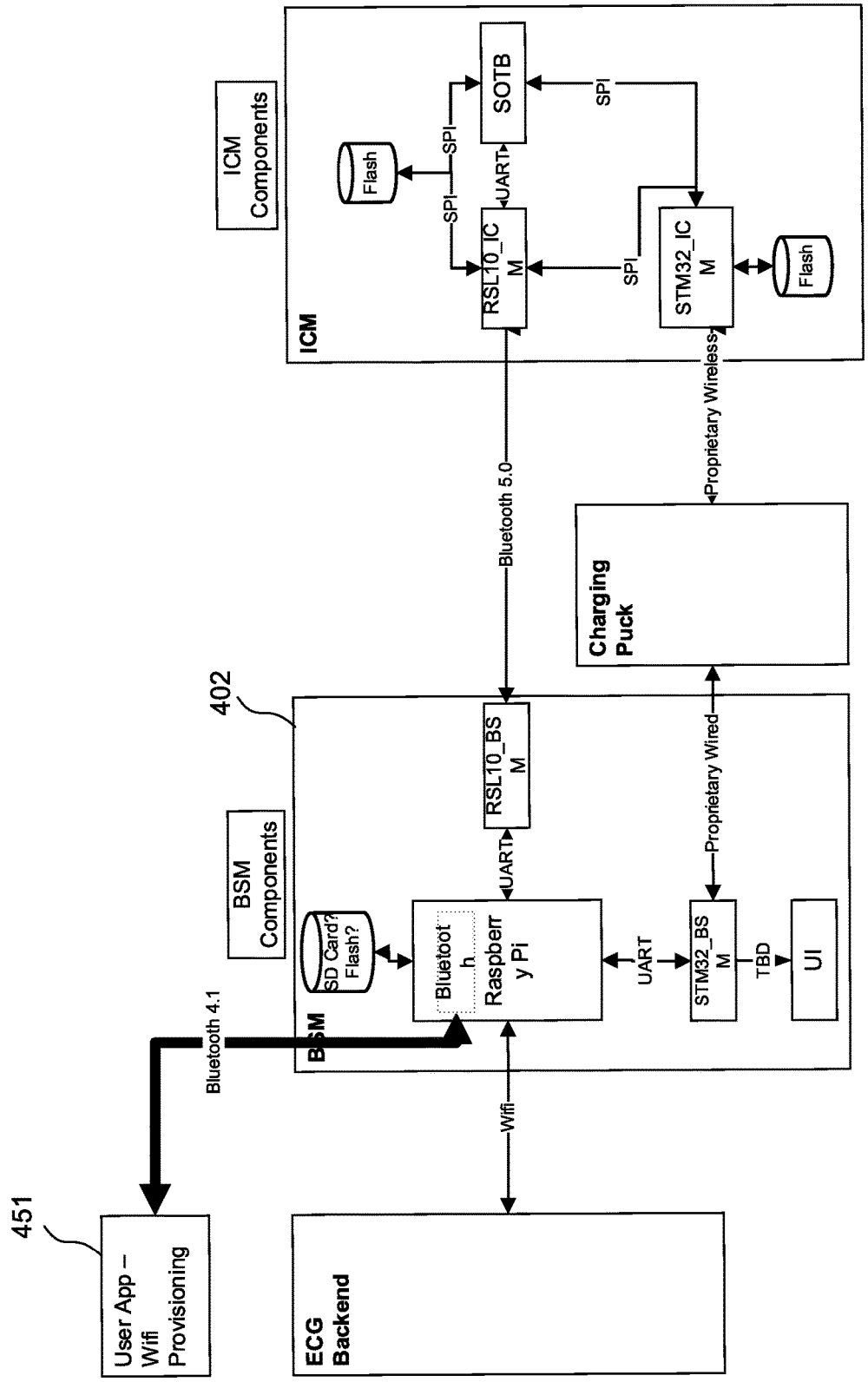
FIG. 26 is a block diagram showing, by way of example, a bedside monitor WiFi provisioning data flow, which is initiated by a user.

Communication can also occur between the bedside monitor and a user application for initiating WiFi. FIG. 26 is a block diagram showing, by way of example, a bedside monitor WiFi provisioning data flow 450, which is initiated by a user. The bedside monitor 402 can indicate available networks for use by the bedside monitor and strength of the networks, as well as a connected status, once available. The user can select a network and enter a password associated with the network to connect with the bedside monitor 402. For instance, upon starting up the bedside monitor, WiFi provisioning can be run to allow the user to set up the bedside monitor by connecting the bedside monitor 402 to a user application 451 via Bluetooth and receiving available networks for WiFi. The user application 451 can obtain information from the ICM for review by or notification to the user.

Figure 27:
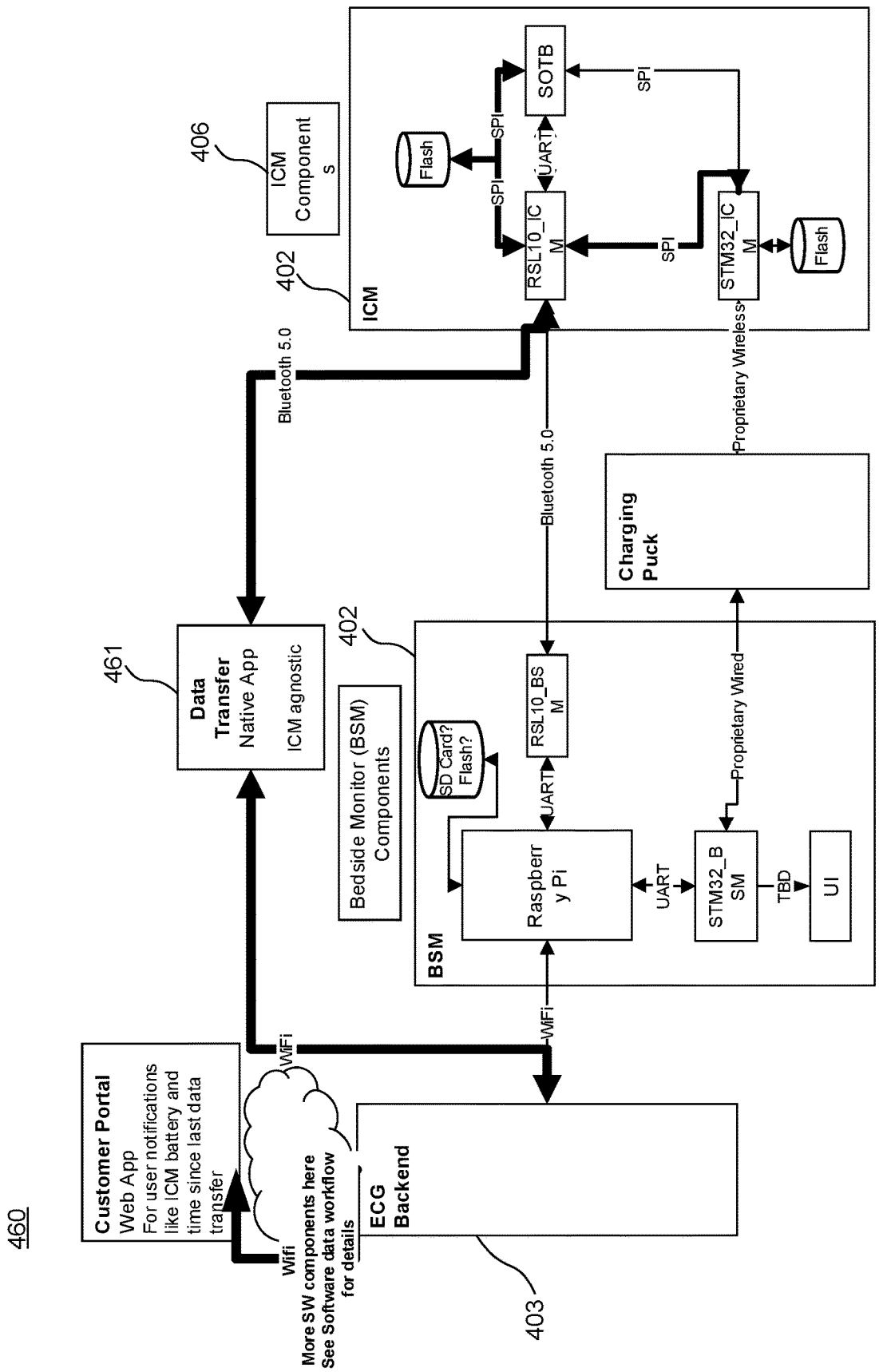
FIG. 27 is a block diagram showing, by way of example, an ICM initiated data flow.

Data collected by the ICM can be transferred to the ECG backend via a mobile application without use of the bedside monitor. FIG. 27 is a block diagram showing, by way of example, an ICM initiated data flow 460. The ICM 402 can provide data to the backend 403 via a mobile phone application 461, instead of via the bedside monitor 402. Specifically, the ICM 401 can provide ECG data, logs from ICM components 406, and status of ICM components 406 to the backend 403 via the application 461, while the backend 403 provides ICM components 406, firmware updates and initial charge parameters to the ICM 401. The application can be specific to a particular ICM or can be used for different types of ICMs.

While the invention has been particularly shown and described as referenced to the embodiments thereof, those skilled in the art will understand that the foregoing and other changes in form and detail may be made therein without departing from the spirit and scope.

What is claimed is:

1. A method for data exchange and charging, comprising:
   monitoring an implantable medical device;
   initiating charging of the implantable medical device by providing charge parameters from the implantable medical device to a bedside monitor, comprising:
   supporting communication between a puck associated with the bedside monitor and implantable medical device; and
   charging of the implantable medical device by the puck using the charge parameters;
   encrypting ECG data collected by the implantable medical device via the puck associated with the bedside monitor;
   simultaneously with the charging, initiating by the puck transfer of the ECG data from the implantable medical device to the bedside monitor; and
   programming the implantable medical device via the bedside monitor.

2. A method according to claim 1, wherein the implantable medical device comprises a supervisor chip to communication with charging circuitry on the puck.

3. A method according to claim 1, further comprising:
   controlling an amount of charge to the implantable medical device by generating a waveform via a communication bus.

4. A method according to claim 1, wherein the transfer of data occurs via a charge waveform or Bluetooth.

5. A method according to claim 1, wherein the implantable medical device comprises a Bluetooth module that communications with a Bluetooth module in the puck.

6. A method according to claim 5, wherein the puck communicates with the bedside monitor via a hardware platform on the bedside monitor.

7. A method according to claim 1, wherein the data transferred from the implantable medical device to the puck associated with the bedside monitor is further transferred to a backend server.

8. A method according to claim 1, wherein further data is transferred from a backend server to the implantable medical device.

9. A method according to claim 1, wherein the transfer of the data occurs at predetermined times or on a daily basis, monthly basis or multiple times a day.

10. A method according to claim 1, wherein the backend server provides the implantable medical device with initial charge parameters.

11. A method for data exchange and charging, comprising:
    monitoring an implantable medical device;
    initiating charging of the implantable medical device by providing charge parameters from the implantable medical device to a bedside monitor, comprising:
    supporting communication between the bedside monitor and implantable medical device; and
    charging of the implantable medical device by the puck using the charge parameters; and
    simultaneously with the charging, initiating transfer of ECG data from the implantable medical device to the bedside monitor;
    maintaining a continuous connection between the bedside monitor and cloud server to transfer the ECG data collected by the implantable medical device from the bedside monitor to the cloud server without authentication.

12. A method according to claim 11, wherein the implantable medical device comprises a supervisor chip to communication with charging circuitry on the bedside monitor.

13. A method according to claim 11, further comprising:
    controlling an amount of charge to the implantable medical device by generating a waveform via a communication bus.

14. A method according to claim 11, wherein the transfer of data occurs via a charge waveform or Bluetooth.

15. A method according to claim 11, wherein the implantable medical device comprises a Bluetooth module that communications with a Bluetooth module in the bedside monitor.

16. A method according to claim 15, wherein the bedside monitor communicates with the bedside monitor via a hardware platform on the bedside monitor.

17. A method according to claim 11, wherein the data transferred from the implantable medical device to the bedside monitor is further transferred to a backend server.

18. A method according to claim 11, wherein further data is transferred from a backend server to the implantable medical device.

19. A method according to claim 11, wherein the transfer of the data occurs at predetermined times or on a daily basis, monthly basis or multiple times a day.

20. A method according to claim 11, wherein the backend server provides the implantable medical device with initial charge parameters.

* * * * *